(12) United States Patent
Shachar et al.

(10) Patent No.: US 9,220,425 B2
(45) Date of Patent: Dec. 29, 2015

(54) METHOD AND APPARATUS FOR MEASURING BIOPOTENTIAL AND MAPPING EPHAPTIC COUPLING EMPLOYING A CATHETER WITH MOSFET SENSOR ARRAY

(71) Applicants: Yehoshua Shachar, Santa Monica, CA (US); Eli Gang, Los Angeles, CA (US)

(72) Inventors: Yehoshua Shachar, Santa Monica, CA (US); Eli Gang, Los Angeles, CA (US)

(73) Assignee: Magnetecs Corp., Ingelwood, CA (US)

( * ) Notice: Subject to any disclaimer, the term of this patent is extended or adjusted under 35 U.S.C. 154(b) by 580 days.

(21) Appl. No.: 13/621,727

(22) Filed: Sep. 17, 2012

(65) Prior Publication Data

US 2014/0081114 A1   Mar. 20, 2014

(51) Int. Cl.
*A61B 5/04*     (2006.01)
*A61B 5/0428*   (2006.01)
*A61B 5/00*     (2006.01)
*A61B 5/042*    (2006.01)
*A61B 5/0478*   (2006.01)

(52) U.S. Cl.
CPC ............. *A61B 5/04001* (2013.01); *A61B 5/042* (2013.01); *A61B 5/04284* (2013.01); *A61B 5/6858* (2013.01); *A61B 5/0478* (2013.01)

(58) Field of Classification Search
CPC ............... A61B 5/0402; A61B 5/0422; A61B 5/04284; A61B 5/0408; A61B 5/04085; A61B 5/042; A61B 5/0478; A61B 5/72–5/7296; A61B 2562/0209; A61B 2562/06; A61B 2017/00053; A61B 2017/00044; A61B 2017/00026; A61B 2017/00022

USPC ......... 600/372–374, 377, 378, 381, 393, 509, 600/544–545

See application file for complete search history.

(56) References Cited

U.S. PATENT DOCUMENTS

| | | | | |
|---|---|---|---|---|
| 3,229,686 | A | * | 1/1966 | Edmark, Jr. ............... 600/502 |
| 5,083,562 | A | * | 1/1992 | de Coriolis et al. ............... 607/7 |
| 5,607,433 | A | * | 3/1997 | Polla et al. .................... 606/107 |
| 6,023,638 | A | * | 2/2000 | Swanson ..................... 600/510 |
| 2004/0015065 | A1 | * | 1/2004 | Panescu et al. .............. 600/374 |
| 2004/0082860 | A1 | * | 4/2004 | Haissaguerre ............... 600/466 |
| 2006/0265039 | A1 | * | 11/2006 | Bartic et al. .................. 607/116 |
| 2007/0093801 | A1 | * | 4/2007 | Behnke ........................... 606/34 |
| 2007/0197891 | A1 | * | 8/2007 | Shachar et al. ............... 600/374 |
| 2010/0160737 | A1 | * | 6/2010 | Shachar et al. ............... 600/202 |
| 2014/0018792 | A1 | * | 1/2014 | Gang et al. ..................... 606/41 |

* cited by examiner

*Primary Examiner* — Lee S Cohen
*Assistant Examiner* — Erin M Cardinal
(74) *Attorney, Agent, or Firm* — Marcus C. Dawes; Daniel L. Dawes

(57) ABSTRACT

This invention relates generally to electro-anatomical mapping method and an apparatus using a catheter and more particularly to a mapping catheter having an embedded MOSFET sensor array for detecting local electrophysiological parameters such as biopotential signals within an excitable cellular matrix geometry, for determining physiological as well as electrical characteristics of conduction path and its underlying substrate within the endocardial and epicardial spaces, the arterial structure and in ganglionic plexus. The apparatus with its MOSFET sensor is geometrically configured as a decapolar linear array and optionally with an 8×8 sensor matrix placed on a balloon-like structure.

13 Claims, 25 Drawing Sheets

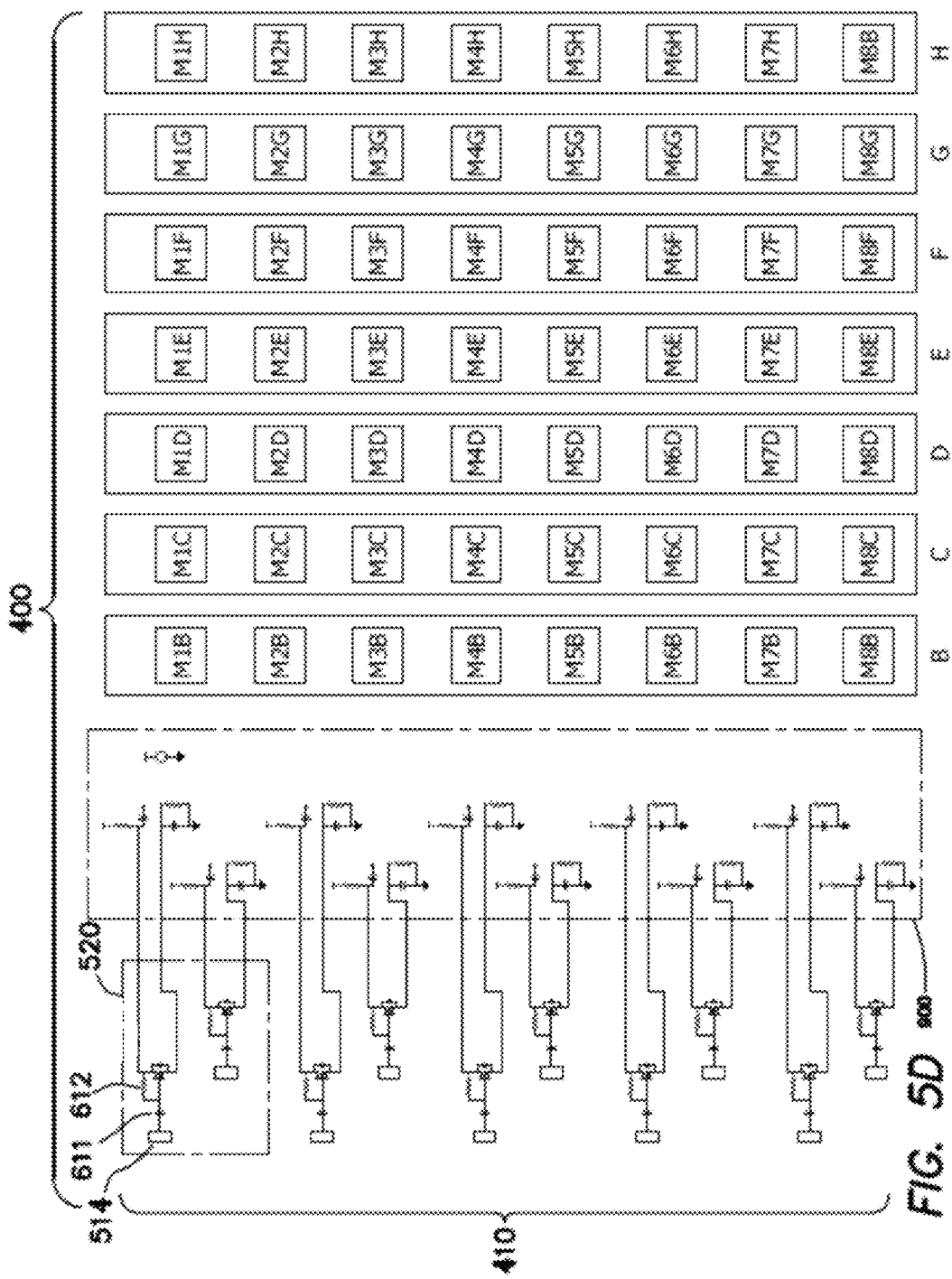

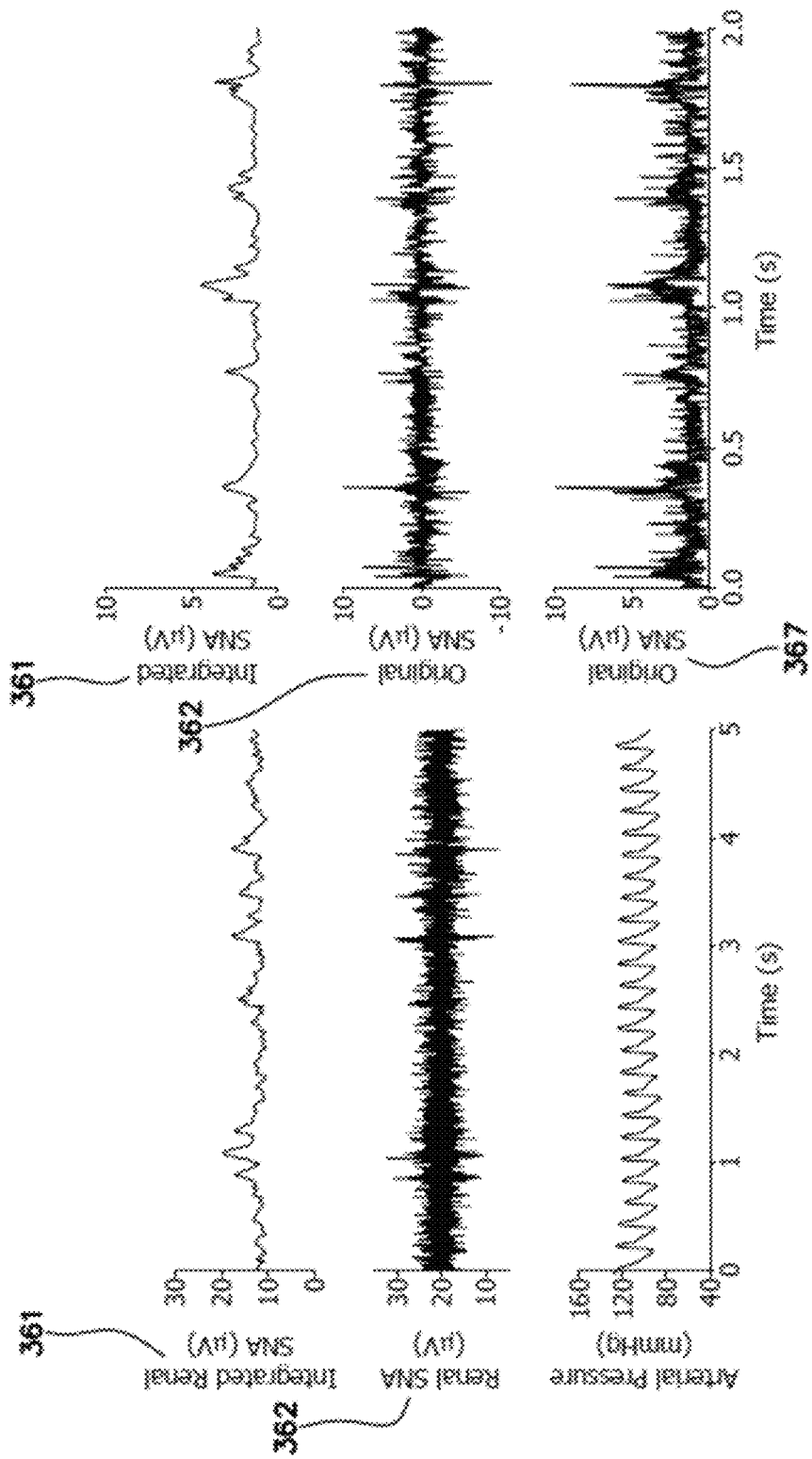

METHOD AND APPARATUS FOR MEASURING BIOPOTENTIAL AND MAPPING EPHAPTIC COUPLING EMPLOYING A CATHETER WITH MOSFET SENSOR ARRAY

FIELD OF THE INVENTION

The invention relates to the a method and apparatus for navigating and recording electrical characteristics of electrophysiological signals using a MOSFET sensor guided by a magnetically-deployable mechanism.

BACKGROUND

"Apparatus for magnetically deployable catheter with MOSFET sensor and method for mapping and ablation," U.S. Pat. No. 7,869,854, filed on Feb. 23, 2006, published as U.S. Pat. Application No. 2007/0197891, assigned to Magnetecs Corporation, which discloses a MOSFET sensor guided by a magnetically-deployable mechanism, is incorporated herein by reference. Corresponding applications include EPO Patent No. 07751190.5; Canadian Patent No. 2637622; and Hong Kong Patent No. 09104053.7.

Nevertheless, there is a great and still unsatisfied need for an apparatus and method for measuring biopotential activity with the use of a MOSFET sensor. This application further improves the efficacy and safety of the procedure by enabling an accurate disclosed method and apparatus which provides for high fidelity sensing of the nerve bundle electrical activity which has a direct measure to the outcome of the procedure efficacy and safety.

The art of electrophysiology studies employs variety of devices, specifically catheters with different electrical configurations of electrodes using magnetic as well as electrical impedance technique to form an electro-anatomical map. Because of its high success rate and low morbidity, radiofrequency (RF) catheter ablation has become a first line treatment for many arrhythmias. In this procedure, one or more electrode catheters are advanced percutaneously through the vasculature to contact cardiac tissues. Radiofrequency energy of up to 50 W for 60 seconds is delivered so as to remodel the electrical path or circuit within the heart chamber.

However, ablation of more complex arrhythmias, including some atrial tachycardias, many forms of intra-atrial re-entry, most ventricular tachycardias, and atrial fibrillation, continues to pose a major challenge. (Paul A Friedman Heart. 2002 June; 87(6): 575-582). This challenge stems in part from the limitations of fluoroscopy and current napping catheter construction and sensory apparatus to locate accurately both the geometry and time domain of the wavefront activity generated by the "avalanche" of the cellular excitable matrix. The inability of the current electrode technology to account for the cellular biopotential transfer with the resolution and the ionic transfer time depicting the actual energetic event is insufficient in the measurement as well as representing the "avalanche" dynamics of this bioenergetic event. This is the main drawback of the existing and prior art relating to "electrode technology".

The drawback noted above, whereby the existing art does not account for the dynamics of the ionic potential with the necessary fidelity which mimics the actual energetic event, is further supported by the use of the "conductor geometry" theory, which represents the cellular path as a cable i.e.: "the cable theory", or the mathematical modeling of bioelectrical current along passive neuronal fibers. Existing hardware employing electrode technology, coupled with the general algorithmic representation of the biopotential dynamics under such theory (both hardware and cable theory) suffer from the limitations which the invention disclosed below solves by the use of the MOSFET sensor array and its method of map reconstruction, as shall be annotated by the figures and their associated description.

In summary, the problem of reconstruction of the electrophysiological activity in the prior art is two-fold: At the one hand it is the results of the use of electrodes and its associated electrical circuit design, and on the other hand it is further handicapped by modeling the biopotential activity as a physical phenomenon whereby excitable cells are modeled by employing the "cable theory" with isotropic behavior. The use of electrodes and cable theory is a good approximation of idealized conditions of such energetic events, but suffers from the inability to associate accurately the intracardiac electrogram with a specific endocardial site which also limits the reliability with which the roving catheter tip can be placed at a site that was previously mapped. This results in limitations when the creation of long linear lesions is required to modify the substrate, and when multiple isthmuses or "channels" are present. Additionally, since in conventional endocardial mapping a single localization is made over several cardiac cycles, the influence of beat-to-beat variability on overall cardiac activation cannot be known.

The need to improve modeling of cellular electrical activity is central to physiology and electrophysiological studies. Biopotential recording and mapping of such electrical activity enables the physician or researcher to form and fashion his or her understanding of the fundamental data gathering and analysis of such diverse biological activities as sensory perception, communication between neurons, initiation and coordination of skeletal-muscle contraction, synchronization of the heart beat, and the secretion of hormones.

Most mathematical models of cellular electrical activity are based on the cable model, which can be derived from a current continuity relation on a one-dimensional ohmic cable. As such, its derivation rests on several assumptions: ionic concentrations are assumed not to change appreciably over the time of interest, and a one-dimensional picture of cell geometry is assumed to be adequate for purposes of describing cellular electrical activity. These assumptions, however, may not hold in many systems of biological significance, especially in the central nervous system and cardiac tissue, where micro-histological features may play an essential role in shaping physiological responses.

The invention and its embodiments, as featured by the use of an integrated MOSFET Sensor Array, solves this and other problems of local definition of reporting on essential electrophysiological parameters, without the compromise noted the prior art, some of which are described by Bin Yin et al US Pat. Pub. 2011/0137200, which describes a system and a method in which an electrophysiological signal is sensed capacitively with at least two closely spaced electrodes such that the electrodes experience strongly correlated skin-electrode distance variations.

Chii-Wann Lin et al in US Pat. Pub. 2010/0145179, describes a high-density micro-electrode array connected to the same conducting wire. Serial switches enable sequential electrical connection of the micro-electrode array.

Paul Haefner in US Pat. Pub. 2007/0293896 describes an arrhythmia discrimination device and method which involves receiving electrocardiogram signals and non-electrophysiological signals at subcutaneous locations. Both the electrocardiogram signals and non-electro physiologic signals are used to discriminate between normal sinus rhythm and an arrhythmia.

These methods have limited success in reaching and reporting on an electro-anatomical site and reduces the ability of the operator to provide a clinically optimal resolution to the problem of identifying accurately the source and its location and further, the prior methods and their exemplified apparatus cannot achieve such precision, and hence results in suboptimal successes of remodeling the heart electrical signal propagation, as well as neuromodulation and their intended clinical outcomes.

BRIEF SUMMARY OF THE INVENTION

The disclosure provides a method and an exemplary apparatus which enables the creation of an electro-anatomical map with fidelity and accuracy depicting a local electrogram with their native dynamics, and their geometrical as well as its time domain specificity, and further providing for reconstruction of the anatomical and etiological characteristics of the cellular matrix which the apparatus surveying. In some embodiments of the technology, a diagnostic study is performed to define the arrhythmia mechanism, and subsequently, an ablation catheter is optionally positioned adjacent to the arrhythmogenic substrate to perform a curative procedure (e.g.: ablation).

The sensory apparatus and method we disclose in this application captures the complexity, as well the time domain of such energetic events, synchronously. The MOSFET sensor array with its fidelity further mimics the underlying dynamics, and will improve conventional catheter based mapping techniques by localizing and identifying precisely the arrhythmogenic substrates that are removed from fluoroscopic landmarks and lack characteristic electrogram patterns.

The disclosed embodiments employ a MOSFET sensor array for the detection and recording of bioelectric potential, as the use of the MOSFET sensor array embedded within a decapolar catheter and/or a balloon catheter. Generally the method includes the steps of first the mapping of the site so as to diagnose and define the relevant optimal location for remodeling of electrical pathways, using methods such as RF, laser and cryo-ablation modalities, and further by applying such methods to provide for neuromodulation of nerve or ganglionic plexus.

The main tenets of the use of transistorized electrodes employing a MOSFET sensor array embedded in a catheter distal end, is to provide a method and an exemplary apparatus for generating an electro-anatomical map that its specificity with reference to the local tissue substrate (within the cardiac chambers) which will reveal the relationship between anatomical characteristics and the corresponding substrate map underlying the muscle tissue. Specifically, we refer to the fact that electrical activity and its vectorial trends are the results of the electrical properties of the underlying substrate, i.e. conductivity (p or $S \cdot m^{-1}$) and with excitable cells and/or fibrotic formations which, if mapped, will enable a physician to diagnose the underlying arrhythmogenic cause of a disease model. This hypothesis is corroborated with the use of the disclosed MOSFET sensor array, as it enables the local mapping of the underlying substrate with its electrical and magnetic components, as shall be shall be demonstrated by the ensuing paragraphs and their accompanying figures.

It is clear to those familiar with the art of electrophysiology mapping, that methods using electrode technologies of all different combinations as noted by the prior art, suffer from the inability to differentiate between signals emanating from "near" and "far fields" as the electrodes in the prior art are typically made of a metal-electrolyte interface. The interface impedance in this relation is represented as a capacitor, and in a non-polarized electrode, the impedance is represented as a resistor. But in practice both capacitive and resistive components are present in the existing art, while the disclosed method and the accompanying apparatus of this invention employ the MOSFET isolated junction, which measures the action potentials without the parasitic capacitive or resistive loads characteristic of the prior art.

In one embodiment of this invention, the apparatus is not dependent on the phenomenological representation of resultant summations of multiple path conduction venues or, alternatively, as a set of complex averages, but provides a true representation of the local conduction path which mirrors the underlying substrate and its fibrotic as well as its excitable path. The aim of the transistorized arrangement is to reveal the true causal relationship between electrical activity and its underlying biological substrate.

In one embodiment, we disclose that cellular etiology does provide us with electrophysiological indications in support of the use of the MOSFET sensor array in assessing and evaluating the signal generated by bioelectric potential as well as direct measurements of nerve and ganglionic activities.

The invention and its embodiments, as featured by the use of an integrated MOSFET Sensor Array, solve this and other problems of local definition of reporting on essential electrophysiological parameters, without the compromises noted in the prior art.

In spite of these many obstacles, the disclosed embodiments have the potential to overcome these anatomic and technical difficulties and further improve the indices of success by reducing unnecessary injury by the use of local monitoring of nerve impulse activity. In one embodiment, the bioelectric signal measurements and the construction of cell and organ electromagnetic field activity maps based on these measurements improves the bioelectric signal measurement, and has a wide range of biomedical application in modeling and diagnostic procedures. The difficulty in the prior art of measurement and mapping procedures mainly relates to the degree with which the measuring tools interfere with the measured bioelectric fields and signals, thus affecting the fidelity of the boundary conditions from which the modeling and diagnostic maps are generated.

In one embodiment, a minimally invasive biosensor technique advantageously applies high impedance and low capacitance semiconductor sensing technology combined with techniques of eliminating the traditional double-layer ionic transfer and conductive charge injection effects. The double-layer ionic transfer and conductive charge injection effects distort the regular electromagnetic fields and activation potentials of the measured tissue. The system can also be used to diagnose conditions of cardiac arrhythmias providing ECG signals for electrocardiographic mapping, and provide EEG signals for the localization and analysis of spontaneous brain activities including the ability of measuring ganglionic bioelectrical activity for pre- or post-operational monitoring.

In one embodiment, the use of high impedance and low capacitance semiconductor sensing technology has the advantages when using the MOSFET sensor array, which is described in the present disclosure and is based on the ability of the apparatus to measure the bioelectric potentials with a substantially improved sympathetic nerve activity (SNA) ratio.

In one embodiment, the measurement is achieved by using isolated FETs based on an integrated MOSFET sensor technology with its differential output, coupled with its high noise immunity and low static power consumption, and provides additional advantages with the static CMOS gates which are very power efficient because they dissipate nearly zero power when idle, hence do not inject additional noise to the tissue.

In other embodiment, the system uses a non-invasive boundary condition sensor technique in which a plurality of measuring devices is embedded on the distal end of a catheter. The measuring devices collect simultaneous signal data sets from the surface of an area covered by the catheter adjacent, for example, to the cardiac tissue or renal artery. The usefulness of the collected data is evident by: (i) the location of the data points and the measured signals (such as, for example, biopotential, pressure and temperature), which provide direct and local values of critical parameters at particular places within the investigated region, and (ii) the data location and signal value-matrices provide the boundary conditions of the patient's tissue so as to compute and map the field and signal propagation and distribution within the volume of the investigated region. In the situation where the arterial structure (e.g. the renal artery) is being monitored, this system advantageously pinpoints the main sources and high intensity loci of spontaneous nerve activity. From the specific data (iii) the physician can monitor particular areas and symptoms, for example, using data from the plurality of the MOSFET measuring devices and (iv) a nerve impulse signal(s) map can be generated by the ensuing description associated with solution to electro-anatomical map formation.

The accuracy of the measurement for both the monitoring and mapping procedures depends on the Minimally-invasive qualities of the MOSFET sensor measuring device. The interface of the present innovation with the active biopotential region is capacitive. The dielectric between the device sense-plate and, for example, the renal artery plexus is an insulating material in the electrolyte of the blood.

In one embodiment, the electrostatic field conditions can be computed for this interface and if the inverse-problem mapping method is used, the system can employ Poisson's and Laplace's formalise, where the measured data serves as the boundary condition for all computations. In cases where brain activity is measured, the system proposed by the invention can change the baseline constants of the dielectric coefficients of the brain tissue, for example: gray matter dielectric constant is about 56 κ; brain's white matter is about 43 κ, while brain's meninges are about 58 κ. Further details of the boundary condition modeling will improve the accuracy of the predictable algorithm when using the apparatus for measuring brain activity. Further specificity of the charge density coefficient of e.g. the cerebro-spinal fluid can be estimated or continuously when measuring for these computations, similarly blood vessel are modeled and set as parameters for comparison when actual measurements are conducted employing the MOSFET sensor array. A practitioner familiar with the art will understand the use of such sensors in measuring the myocardial biopotential activity.

In cases where modeling of the bioelectric activity of nerve impulse and/or excitable cellular matrix in the endocardium we employ the Poisson's Equation, which teaches that the electrostatic field in a material with dielectric and charge properties is:

$$\frac{\partial^2 V}{\partial x^2} + \frac{\partial^2 V}{\partial y^2} + \frac{\partial^2 V}{\partial z^2} = \frac{\rho_v}{\varepsilon} \qquad (1)$$

Where $\rho_v$ is the measured volume charge density, and
i. Is the average dielectric constant Known solutions of partial differential equations fitting the Poisson's Equation is performed to obtain the electrostatic field distribution along the surface area of the measurement site and/or the field map within the tissue.

Laplace's Equation describes for the charge-free insulation layer of the sensing array:

$$\frac{\partial^2 V}{\partial x^2} + \frac{\partial^2 V}{\partial y^2} + \frac{\partial^2 V}{\partial z^2} = 0 \qquad (2)$$

The solution methods, using the boundary condition locations and measured signal values are similar to the Poisson's Equation. Other numerical solutions may employ a known differential equation which results in a minimum error for the boundary conditions.

In one embodiment, the MOSFET sensing by the electrode surface has an insulated silver (or platinum) plate to sense the facing tissue electrostatic field. The electric field intensity between this plate and the tissue is optionally calculated from the Poisson's Equation and is further simplified for the case of two parallel plates representing the capacitor formed by the insulated sensing plate, and the tissue, at distance d.

$$E_d = \frac{\rho_v \cdot d^3}{3 \cdot \varepsilon} - \frac{\rho_v \cdot d^2 \cdot d_0}{2 \cdot \varepsilon} + \frac{\rho_v \cdot d_0^3}{12 \cdot \varepsilon} \quad [\text{V/m}] \ d \geq d_0. \qquad (3)$$

i. Where $d_0$ is the minimum distance defined by the insulation layer.

In one embodiment, however, using any of these methods requires accurate boundary condition measurements which produce minimum error due to the measurement itself. The present disclosure describes measuring techniques which enable such measurements.

In one embodiment, a MOSFET having a matrix formed of sensors embedded therein is described which directly measures the local biopotential with its fractionated and continuous signals, analyzes such bioelectrical potentials and displays a measurement.

In other embodiment, a MOSFET array sensor system is fitted with an analyzing module for processing bioelectric signals so as to render a predictive value relative to the viability of the local tissue sampled by the apparatus is disclosed.

In an embodiment a monitoring system for displaying measured parameters such as bioelectric potential, pressure as a measure of impedance, temperature, and impedance of the tissue underlying the MOSFET sensor array is disclosed. The sensor embedded in the catheter can take the form of any of several sensing devices which directly measures a parameter indicative of cellular metabolism, tissue blood flow, or tissue oxygenation as it is reflected by its electrical equivalent values through capacitive, conductive, and or resistive processes.

In an embodiment, a plurality of sensors is strategically mounted in a matrix like arrangement so as to monitor various parameters, such as, for example, surface tension, blood flow, tissue metabolism, bioelectric potential, EEG, or the like.

In an embodiment, the signal processing unit can be a multi-channel processor combined with a matrix array sensor. The signal processor is configured to convert the signals from the sensors from an analog signal to a digital signal using an ADC, digitizer, serializer and/or a buffer.

In an embodiment, the signal is amplified and fed to a display unit which may be a strip chart recorder, CRT or LCD display.

Other objects, features and advantages of the present invention will become apparent from a reading of the following detailed description and appended claims when taken in conjunction with the accompanying drawing.

BRIEF DESCRIPTION OF THE DRAWINGS

FIG. 5D is a schematic diagram of the 8×8-Polar MOSFET array catheter with its electrodes and power circuitry.

FIGS. 6A & 6B are graphs of the electro-anatomical signals of the renal plexus using an embodiment of the invention.

Figure 1:
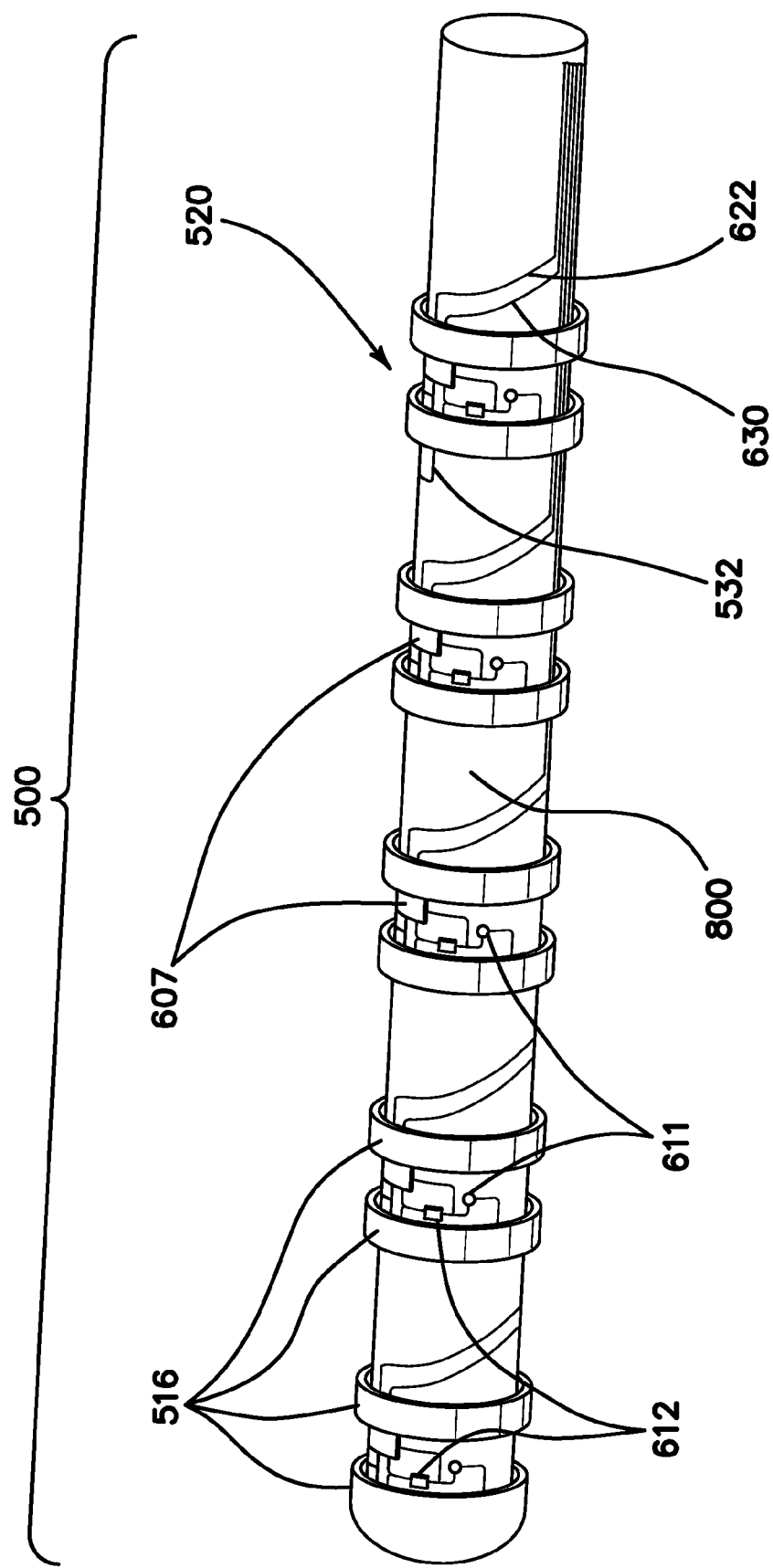
FIG. 1 is side perspective view of a decapolar catheter fitted with a MOSFET sensor module in an array format.

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole. Additional objects and advantages of the current invention will become apparent to one of ordinary skill in the art upon reading the specification.

The accompanying figures, in which like reference numerals refer to identical or functionally-similar elements throughout the separate views and which are incorporated in and form part of the specification, further illustrate the present invention and together with the detailed description of the invention, serve to explain the principles of the present invention.

DETAILED DESCRIPTION OF THE PREFERRED EMBODIMENTS

FIG. 1 is an autographic representation of a decapolar catheter formed with the disclosed MOSFET Sensor Array 500 for measuring bioelectric potential for example, while performing electrophysiological studies within the endocardial tissue. The assembly is comprised of a series of typical electrode rings 516 shown in a decapolar configuration. This layout can be configurable in any combination suitable to those familiar with the art while employing the device while measuring bioelectric potential in a biological media or environment. Electrodes 1A 516 are coupled to a sensor module 520 including a capacitor 611 and resistor 612 which form an electrical unit coupled to a MOSFET 607. The discrete electronic components are mounted on a flexible substrate such as anisotropic conductive film (ACF), mechanically reinforced by the catheter structure 800 formed of polyurethane or silicone, etc. materials commonly used in such construction. The electrical circuit is formed with ground leads 532, power leads 630 and its output 622 connections.

In one embodiment, we cite the electrophysiological studies conducted by Dipen Shah, et al ("Electrophysiological evaluation of pulmonary vein isolation", Europace, 2009, 11-11), as a justification for the use of the disclosed technology in improving the shortcomings and sub-optimal results generated by existing mapping catheters as described in that article. The observations provided by this and many nth papers, points to the fact that identifying complex arrhythmogenic causes requires an electro-anatomical mapping with a resolution and accuracy not currently attainable by previous electrode technology. This application teaches that using transistorized electrode pads (e.g. using MOSFETs) with a local amplifier will substantially advance the art of electrophysiological studies, and provide for better resolution in a temporal domain of the waveform characteristics while distinguishing "far-field" from "near-field" sources, resulting in improved identification of local arrhythmogenic causes. The abstract of the above article notes that " . . . Additional unnecessary ablation and possibly complications can be avoided by the recognition of non-pulmonary vein (non-PV) myocardial contributions to pulmonary vein (PV) electrograms, . . . " And the authors explain that " . . . The posterior wall of the left atrial (LA) appendage contributes far-field electrograms to recordings from all left superior PVs (LSPV), the low lateral LA to 80% of left inferior PV (LIPV) recordings and the superior vena cava to 23% of right superior PV (RSPV) recordings. Each of these far-field components can be recognized in sinus rhythm as well as during ongoing atrial fibrillation by the disclosed apparatus and methods. Finally, the creation of temporally stable and definitive PV isolation remains a currently unsolved problem". The study further states that . . . "A precise understanding of the electrical activation of the PVs and of the neighboring atrial structures forms the basis of the electrophysiological evaluation of PV isolation. Rigorously verified PV isolation is a cornerstone of catheter ablation for atrial fibrillation (AF). Prompt recognition of non-PV electrogram components can prevent unnecessary radio frequency (RF) ablation and may even reduce complications such as PV stenosis and phrenic nerve palsy. The use of the disclosed MOSFET sensor array 500 solves these and other problems noted by the study.

Figure 1A:
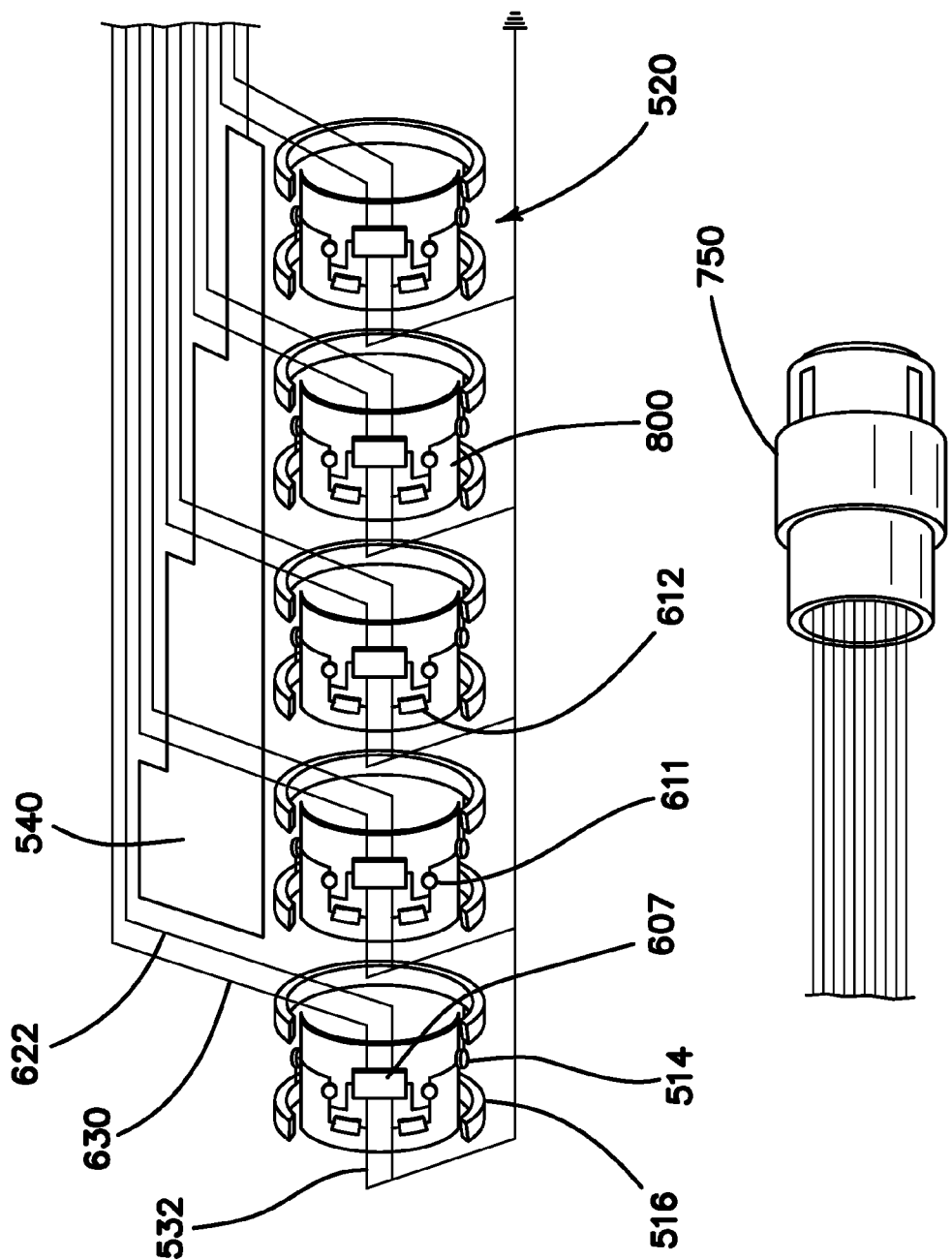
FIG. 1A is perspective diagrammatic exploded view of a decapolar catheter configured as a 5-bipolar node with its wiring end connector.

FIG. 1A depicts an exploded isometric view of a decapolar catheter configured as five bipolar differential signals 580 (not shown in FIG. 1A), and ten unipolar signals (not shown in FIG. 1A) formed at the sensor module 520 nodes. The entire electronic node array is mounted on the underlying polymer catheter structure 800, the sensor electronics includes a resistor 612, capacitor 611, and MOSFET 607 connected to electrode rings 516 for the signal capture. The sensor module 520 is shielded with a ground plane 540, and includes ground leads 532, the power leads 630 and output leads 622 connected to an external molded multi-pin male connector 750. This geometry and layout of the electrode pad 514 and its associated electrode ring 516 on a catheter shaft is optional and can be variously configured based on application according to the teachings of this disclosure.

Figure 1B:
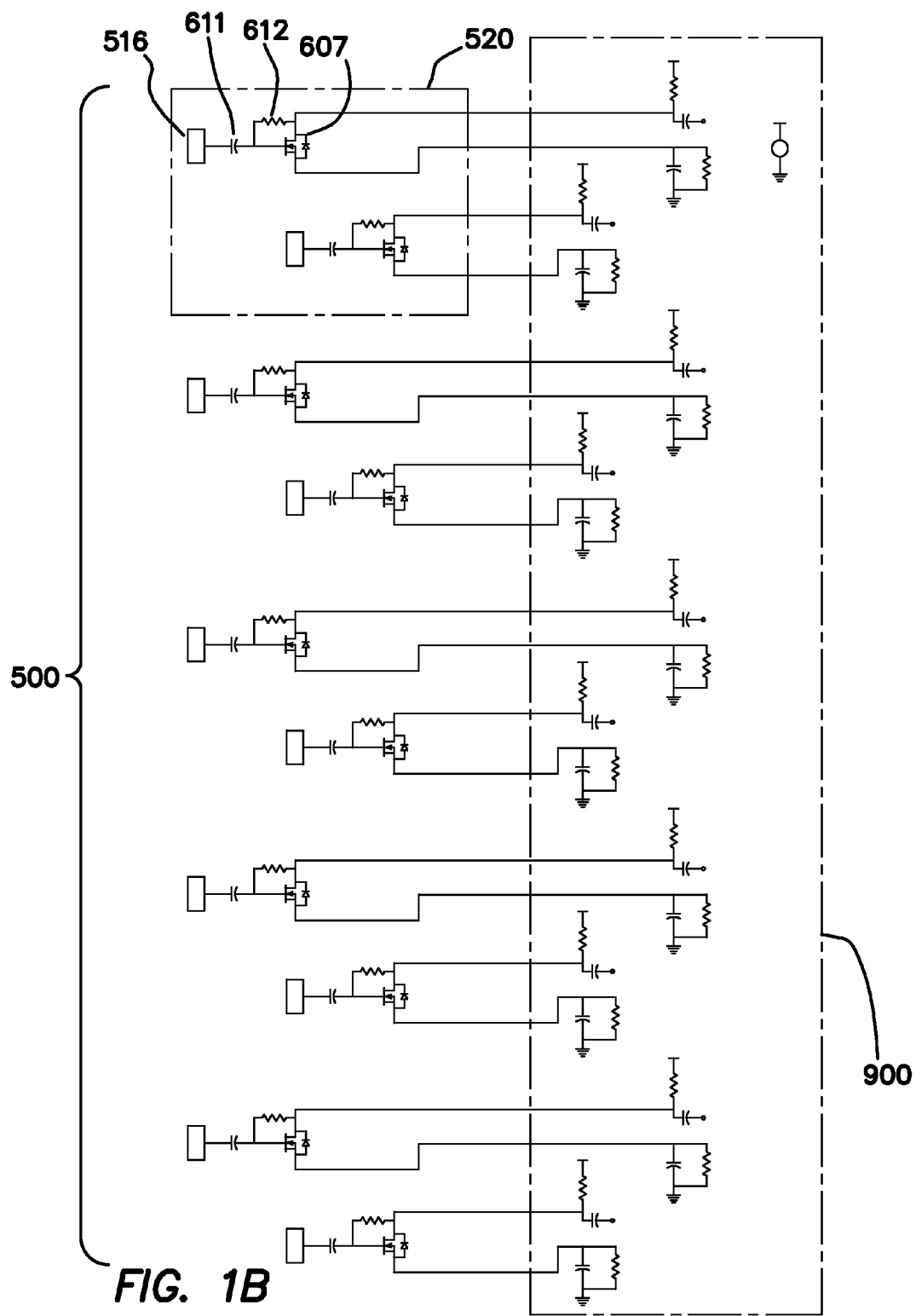
FIG. 1B is a circuit schematic of the decapolar catheter with its electrodes and power circuitry.

FIG. 1B is a schematic representation of a diagnostic catheter with its preferred embodiments comprising of its MOSFET sensor array 500 which acts as a transistorized electrode. The figure describes an array of electrode pads 514 connected to MOSFET common-source amplifiers 607. A high impedance resistor 612 between the gate (G) and drain (D) terminals of the MOSFET biases the transistor in active mode. A resistor 612 and capacitor 611 between the source (S) and ground improve and stabilize small-signal gain of the circuit. Capacitors 611 between the gate (G) and the pad, and the drain and load isolate the DC signal and ensure the small-signal (AC) amplification of the sensor module 520.

The figure further depicts the basic configuration of a platinum electrode pad 1A 616 connected to a capacitor (1 µF) 611 which provides the variable gain (G) on MOSFET (such as noted by the exemplary use of 2N7002) 607 with its resistor (1 M) 612.

The sensor module 520, forms an element in a matrix to enable an architecture of the MOSFET sensor array 500 comprising of n-tuple arrangements of <8, 12, 16, 32, 64, 128> members) of the basic sensory inputs from a biological tissue or nerve ending firing or a summation of ganglionic plexus electrical activity.

The details of operation and the principles that govern the disclosed circuit are illustrated by the figures and their accompanying descriptions which demonstrate the improvements of signal fidelity of the proposed arrangements over the existing art which employs electrode technology to capture the unipolar or bipolar 580 characteristics of the bioelectric potential, and where the ability of the existing electrode art to record electrical values of 1-2 microvolts of biopotential are limited by the physical inability to differentiate the integrated SNA signals of the systolic wave onslaught as well as the "far field" propagation of multiple signals originating from the various ganglionic sources. The difference in resolution provided by the proposed technology of the MOSFET sensor array 500 is the difference between a single static image generated by the current electrode technology verses an impedance spectroscopy, revealing the entire dynamic of the wavefront characteristics in the time domain.

In other embodiments of the use of transistorized MOSFET pads gives rise to the ability to measure local potential of a spatia-temporal event without the compromise associated with the averaging of a signal and where near field response verses far field response are registered. It, should be recalled that when biopotentials in a beating heart are measured, the near field signals for any given sensor will fluctuate significantly more than the far field signals for that given sensor. Hence, the temporal fluctuation of the signals can be processed to differentiate between near and far field signals at any given sensor provided that the sensitivity is high enough so that the small near field signals are not swamped by the far field signals. According to the illustrated embodiments a sensor sensitivity of 0.1 µV or better is sufficient to allow this type of differentiation to occur without signal loss, although typical signal magnitudes are of the order of 4 µV. Further, movement of the catheter, and hence sensors, relative to the measured tissues, provides for another means of differentiating between near and far field signals even in applications here the measured tissue itself is substantially stationary. A further use of transistorized MOSFET pads is to employ the device in recording transmembrane ionic current flow, a bioelectric event which necessitates a fast, local and dynamic registration of the "electrical avalanche" characteristic of such biological phenomenon and further to enable the recordings of current flow distribution in extracellular space.

In another embodiment of this application, the use of the MOSFET sensor array 500 is to solve many diagnostic dilemmas associated with existing methods for the mapping of electro-anatomical signal as well the temporal origin of bioelectrical activities, to be deciphered without the contributions of far field events which contemporaneously mask the true nature of the wave front, leading to erroneous diagnoses. The proposed transistorized electrode technology with its spatiotemporal local and precise differentiation of the origin, time, intensity, frequency and multiple other matrices, is a marked advantage of the invention.

Figure 1C:
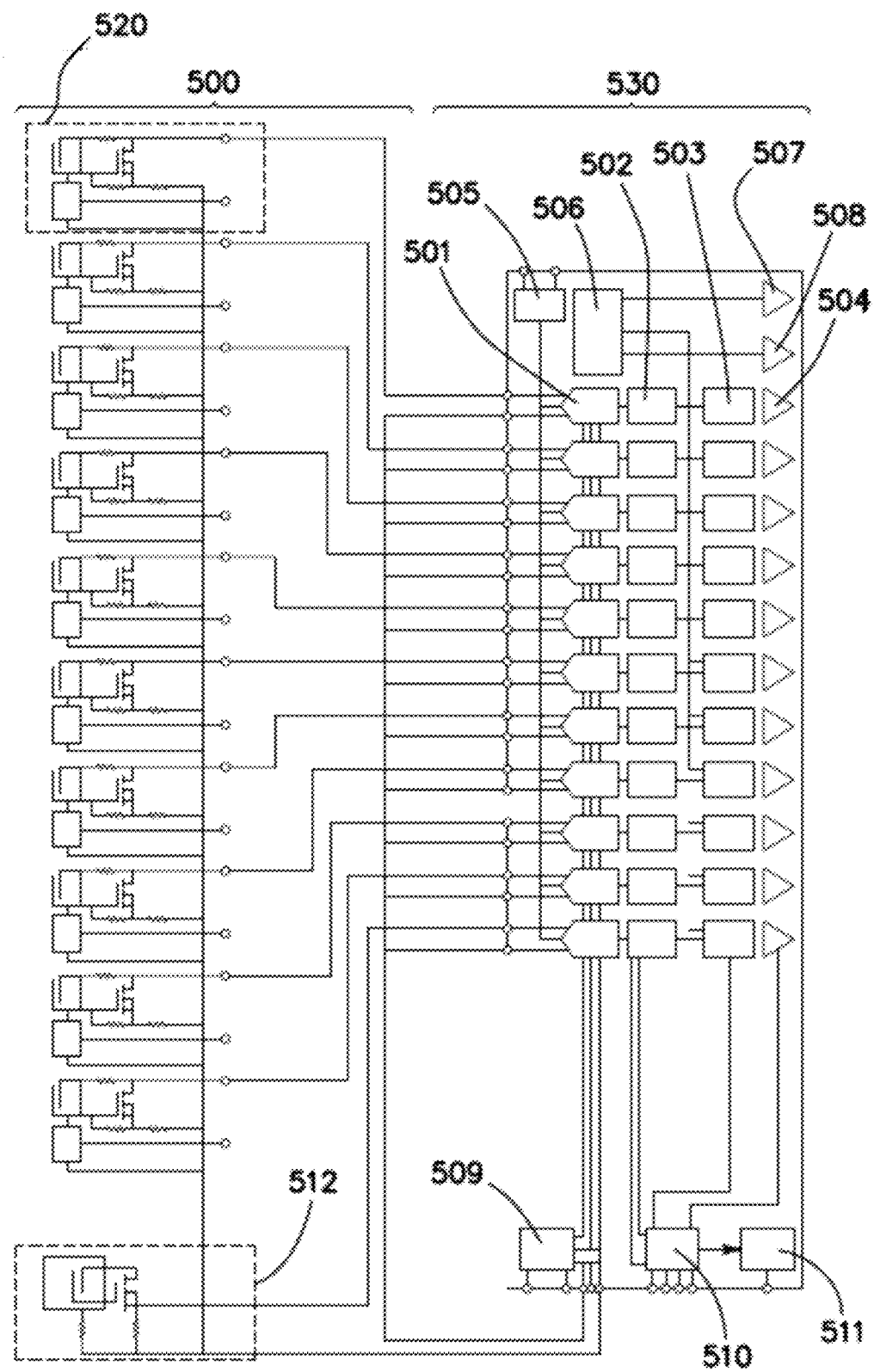
FIG. 1C is a circuit block diagram of the MOSFET sensor array matrix with its associated circuitry for digital signal processing.

FIG. 1C is a schematic outline of the MOSFET sensor array 500 residing on the distal end of the catheter shaft 800 depicting an architecture which enhances the sensor module 520 by demonstrating the ability of the circuit to capture, record, and analyze the bioelectric-potential data generated from a local site and transmitted to a signal processor 530 without the degradation associated with the prior technology.

The system architecture is comprised of three blocks. One of the blocks is a multi-channel integrated MOSFET sensor array 500. The MOSFET sensor array 500 includes sensor modules 520. Sensor modules 520 include an optional pressure transducer with its extended MOSFET gate, a biopotential detector employing a MOSFET gate, and with an optional temperature sensor. The circuit of the combined three sensors and its configuration are identified by reference designator 520. The MOSFET sensor array 500, is linked to a calibration element 512. The calibration element 512 has another MOSFET gate with a fixed value at a nominal potential. The difference between the sensor module 520 and the reference element 512 provides the output. The integrated sensor array outputs are fed to the signal processor 530 of the system. The signal processor 530 includes an analog-to-digital converter (ADC) 501, a digitizer 502, a serializer 503, an output driver 504, a clock buffer 505, a phase lock loop 506, a clock buffer

1 and #2 507, 508 respectively, a reference 509, set registers 510, and ADC controls 511. In summary the integrated sensor array 500 is connected to an ADC through a signal processor 530. The advantage of such an embedded MOSFET sensor array is clear to those familiar with the art, as is described by the detail description of its intended operation and specifically its use in identifying the precise site of a biopotential activity and the sensor ability to discern "near field" from "far field" signals.

Figure 1D:
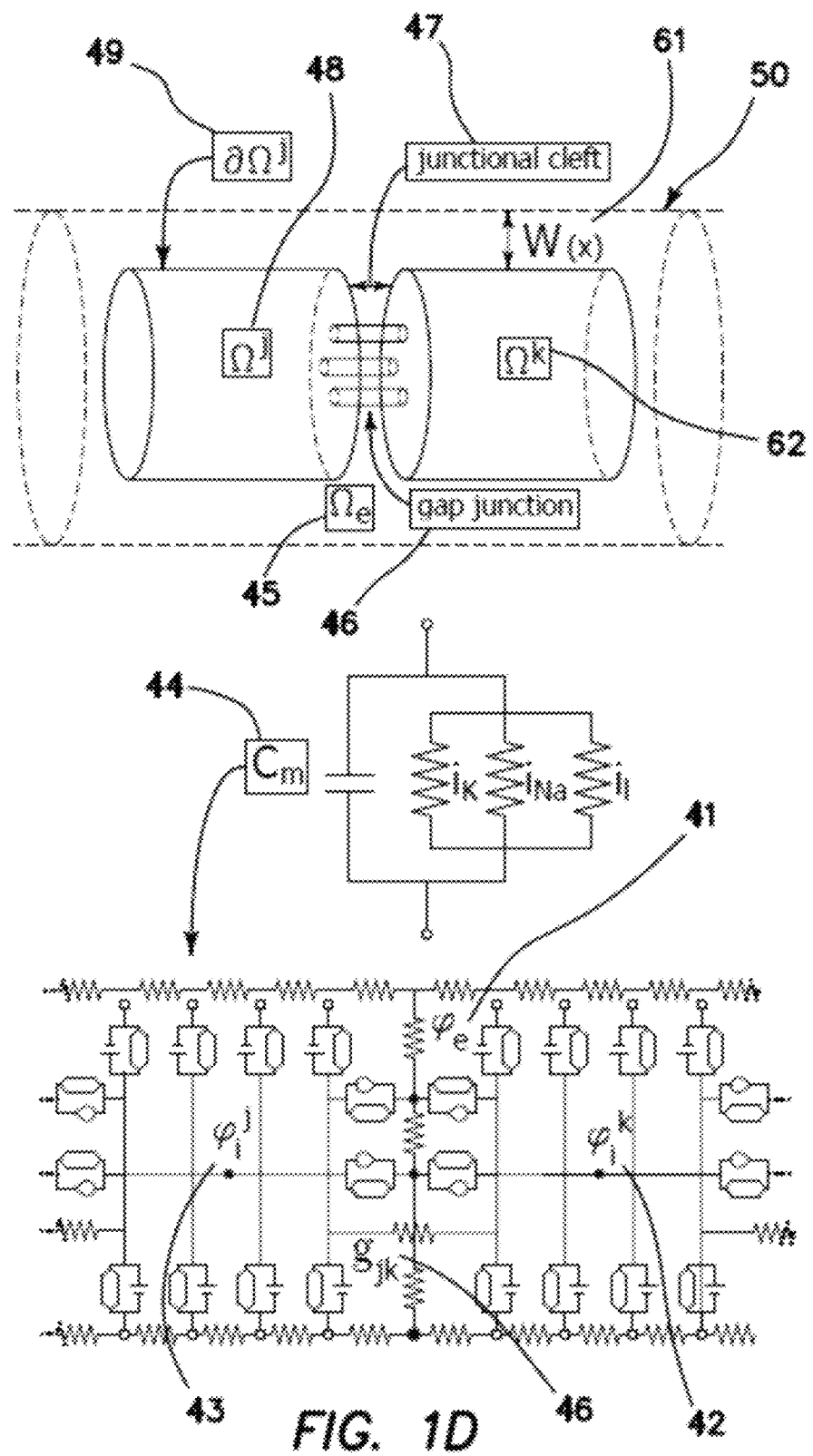
FIG. 1D are diagrams of the cellular conductance modeling of electrical activity in myocardial tissue capturing the effects of ephaptic coupling.

FIG. 1D is a schematic representation of the cellular conductance modeling of electrical activity in myocardial tissue capturing the effects of ephaptic coupling. The need to assess the prior method(s) and apparatus of electrode technology is two-fold. At the one hand is the accuracy and resolution improvements associated with the MOSFET technology, which is the aim of any theory and or scientific observation, but as such the disclosed MOSFET sensor array technology would be recognized as an improvement on the art of electrophysiological studies, we rather contend that the use of the MOSFET sensor array is important, if not necessary for uncovering the arrhythmogenic cause in a complex arrhythmia, where the conduction path and signal velocity represented by the prior method of electrode technology cannot account for the secondary effect of the ephaptic coupling as well as the magnetoelectrogram propagation within the cellular matrix. "Ephaptic coupling" refers to the coupling of adjacent (touching) nerve fibers caused by the exchange of ions between the cells, or it may refer to coupling of nerve fibers as a result of local electric fields. In either case, ephaptic coupling can influence the synchronization and timing of action potential firing in neurons and excitable cellular paths. The argument on the nature and effect of magnetoelectrogram propagation is extensively reviewed and modeled by Shachar, et al, U.S. Pat. No. 7,869,854, where a mapping catheter is described which includes a MOSFET sensor array providing better fidelity of the signal measurements as well as data collection and reduces the error generated by spatial distribution of the isotropic and anisotropic wavefronts.

In one of its embodiment the above patent further describes a system for forming maps depicting the change in potential in the vicinity of an activation wavefront. In other embodiments, the mapping system tracks the spread of excitation in the heart, with properties such as propagation velocity changes. In one embodiment, an interpolation algorithm tracks the electrogram data points to produce a map relative to the electrocardiogram data. As we review the data generated by the prior method(s) and its proliferated electrode variations of catheters, be it bipolar, quadripolar, decapolar, or multi-electrode basket-type geometry, we observe that the need to provide higher-resolution and sampling rate supplementing the pre-existing electrode technology is essential as in the cases of complex arrhythmogenic causes mapped by the prior art electrode technology, where we are unable to accurately capture the dynamics and complexity of the wave front propagation. Our aim in proposing the disclosed MOSFET sensor in an array form(s) is to address a more fundamental problem in the art of electrophysiology-measurement, where cases with complex dynamics of bioelectrical events are present. To illustrate these facts, this application cites a paper describing the effects of ephaptic coupling with its formalism. The paper describes two observational phenomena relating to the needs to capture energetic events which the prior technology cannot fully account for, and further supporting the needs to employ the proposed MOSFET sensor technology in conducting electroanatomical studies.

The inability of the prior electrode technology to address the dynamics and resolution of such energetic events (forming the electrical circuit of the heart cycle), suffers from the inability of the prior art to account for ephaptic coupling and the physical influence of the magnetoelectrogram propagation. The energetic event represented by the electrical circuit of the heart (the cable theory) is described by an ionic potential, as it is traveling through its conduction path of the excitable cells. The figures and the accompanying descriptions will provide an additional support for the use of the MOSFET sensor array as the preferred modality for capturing and identifying the cause(s) in a complex arrhythmogenic disturbance. The inherent circuit formation of the prior art, suffers from the limitation where the ground potential and its amplifier are located at distance from the biopotential activation site (origin) resulting in poor SNA effects, coupled with the signal fidelity which synchronously is compromised by the "averaging" of mixed signals, emanating from "far" and "near field" sources. These and other limitations described by the prior art, including the growing body of clinical observations cited by the medical literature, are the cause, why the prior electrode technology cannot account for the cellular biopotential transfer or dynamics of the wave front accurately. These factors coupled with limited resolution of the prior art, are the main drawback of electrode technology in accounting for the "ionic transfer time domain" (represented by a conditions defined as "avalanche" dynamics of this bioenergetics event.

Using electrode technologies with its different combinations of electrodes, noted by the prior art, users suffer from the inability to differentiate between signals emanating from "near" and "far fields" since the electrodes in the prior art are typically made of metal-electrolyte interface. The interface impedance in this relation is represented as a capacitor, and in a non-polarized electrode, the impedance is represented as a resistor. But in practice both capacitive and resistive components are present in the existing art. Existing models of electrical activity in myocardial tissue are unable to easily capture the effects generally defined as "ephaptic coupling" (PNAS Dec. 7, 2010 vol. 107 no. 49 20935-20940).

Homogenized models do not account for cellular geometry, while detailed spatial models are too complicated to simulate in three dimensions. Here we propose a unique model and disclose apparatus that accurately captures the geometric effects of the cellular ionic dynamics of the biopotential transfer, including a data capture of such activity, and with computationally efficient methodology, which the MOSFET sensor array can solve.

We use this apparatus to enable modeling of such effects by capturing the changes in extracellular geometry, gap junctional coupling, and sodium ion channel distribution on propagation velocity by using a MOSFET sensor array. In support of previous studies, we teach in this application that the use of local amplifier in the form of a MOSFET sensor module, the disclosed apparatus and its algorithmic approach enable the capture of ephaptic coupling by further defining the propagation velocity at low gap junctional conductivity and report on propagation velocity.

This application also finds that conduction velocity is relatively insensitive to gap junctional coupling when sodium ion channels are located entirely on the cell ends and cleft space is small. The numerical efficiency of this model, verified by comparison with more detailed simulations, allows a thorough study in parameter variation and shows that cellular structure and geometry has a nontrivial impact on propagation velocity. This model can be relatively easily extended to higher dimensions while maintaining numerical efficiency and incorporating ephaptic effects through modeling of complex, irregular cellular geometry. Existing homogenized models, while computationally accessible, are not able to deal with the effects of micro-domains as the data generated by the existing electrode technology is insufficient in capturing the dynamics of such bioelectric events. The bioelectric potential is a time domain-dependent event whereby the ionic flux transfer cannot be captured by the prior technology, as it cannot distinguish between far and near field attenuations due to limited bandwidth.

These limitations are solved by the use of the system 600 with its MOSFET sensor array 500 which provides for the physical signal distinction between "near field" and "far field" due to the ability of the system to distinguish the emanation of biopotential from localized anatomy, and from the surrounding corporal structures. Whereas a near-field potential waveform has clear changes in amplitude, polarity, wave shape and/or latency when the position of the active electrode is changed over a small distance, conversely, in the far-field the signal characteristics are not changed by moving the electrode position, hence the far-field signal component is a non-moving potential, further elaborated in FIG. 6C. The MOSFET sensor solves such and other limitations and hence captures the effects of ephaptic coupling "far field" and "near field" crosstalk.

Here we present a model that captures the effects of the intricate cellular geometry with simplifications that will allow the model to be extended more readily to three dimensions while maintaining computational efficiency. With this model we expect to be able to study the effects of changes in geometry (for example, due to hydration or dehydration, medication induced cellular impedance variation etc.) and pathology (such as ischemia) on propagation velocity.

The classical derivation of the equations for action potential propagation makes use of Cable Theory, in which the extracellular resistance is assumed to be isopotentially zero and the intracellular space conductivity is taken to be proportional to the cross-sectional area of the cell. We cite the research article published by Joyce Lin and James P. Keener (published in PNAS Dec. 7, 2010 vol. 107 no. 49 20935-20940), describing a revision to the existing models of electrical activity in myocardial tissue which is unable to capture the effects of ephaptic coupling. The proposal of employing a unique model that accurately captures the geometric effects is due to the fact that with the use of the MOSFET sensor array the simplification of the computational and efficient modeling of the ionic avalanche dynamics is attainable without the use of a complex three dimensional rendering. The native data generated by the MOSFET sensor module need not be manipulated from the information gap extrapolation required in generating a mapping of electro-potential dynamics, as well as isochronal representation, where a three dimensional map of electro-potential in the endocardium is shown on a bit-by-bit basis, and where localized sites of origin of premature beats are reconstructed with their activation sequence.

This application employs the modeling of the effects of changes in extracellular geometry, gap junctional coupling, and sodium ion channel distribution on propagation velocity in a single one-dimensional strand of cells in order to exemplify the limitations of the prior art of electrode technology. In one embodiment while studying the primary as well as secondary effects, be it magnetic wave propagation and/or the ephaptic coupling, this model, verified by comparison with more detailed simulations, shows that cellular structure and geometry has a nontrivial impact on propagation velocity.

In this application we follow the authors and the clinical observations in setting the formal representation and the assumptions which form such modeling. Referring to FIG. 1D the jth cell 49 occupies the space $\Omega j$ 48. The extracellular space 50 the complement of intracellular space; however because this generally quite thin, we view extracellular space as the two dimensional surface of three dimensional cells, hence the extracellular space 50 is defined by 45 $\Omega_e = \cup j \partial \Omega j$. The junctional clefts 47 are part of extracellular space. For each point x in the extracellular space there are $\kappa(x)$ adjoining cells specified by the index set E(x). For x on the boundary of the tissue, $\kappa(x)=1$, and otherwise $\kappa(x)=2$. Similarly, each cell has neighbors to which it is coupled by gap junctions 46, denoted by the indices lj. The gap junctional coupling strength between cell j and its neighbors 62 by gjk(x) for $k \in lj$ and $g_{jk}$ can be nonzero only for x such that cells j and k are adjoining (this assumption is well within the cable theory approach to cellular conduction). The membrane capacitance 44 is denoted by Cm, extracellular conductivity by Ce, extracellular width 61 by W(x), ionic currents by $I^j_{ion}$, intracellular potential 43 by $\phi^j_i$, and extracellular 41 potential $\phi_e$. The right portion of the figure represents an equivalent circuit diagram of the model in the left portion of the figure with the electrical components of resistors and capacitors modeling the energetic event with an idealized geometrical and discretized electrical notation as shown in the right portion of the figure.

Current conservation in the extracellular space represented by the extracellular potential $\phi_e$ 41 is $$-\nabla \cdot (W(x) C_e \nabla \phi_e) = \sum_{j \in E(x)} \left( C_m \frac{\partial}{\partial t} (\phi_i^j - \phi_e) + I_{ion}^j (\phi_i^j - \phi_e, x) \right). \quad [1]$$

The current conservation in the intracellular potential 43 and 42 respectively is $$\chi^j C_m \frac{\partial \phi_i^j}{\partial t} - C_m \frac{\partial}{\partial t} \int_{\partial \Omega j} \phi_e dx + \int_{\partial \Omega j} I_{ion}^j (\phi_i^j - \phi_e, x) dx = \quad [2]$$

$$\sum_{k \in lj} \int_{\partial \Omega j} g_{jk}(x) (\phi_i^k - \phi_i^j) dx,$$

Where $xj = \int \partial \Omega j \, dx$ is the total surface area of the jth cell. Rearranging and simplifying the expression, $$\kappa(x) C_m \frac{\partial \phi_e}{\partial t} - C_m \frac{\partial}{\partial t} \sum_{j \in E(x)} \phi_i^j = \quad [3]$$

$$\nabla \cdot (W(x) C_e \nabla \phi_e) + \sum_{j \in E(x)} I_{ion}^j (\phi_i^j - \phi_e, x).$$

$$\chi^j C_m \frac{\partial \phi_i^j}{\partial t} - C_m \frac{\partial}{\partial t} \int_{\partial \Omega j} \phi_e dx = \quad [4]$$

$$\sum_{k \in lj} \int_{\partial \Omega j} g_{jk}(x) (\phi_i^k - \phi_i^j) dx - \int_{\partial \Omega j} I_{ion}^j (\phi_i^j - \phi_e, x) dx.$$

we obtain the result that the author indicates. This model, verified by comparison with more detailed simulations, shows that cellular structure and geometry has a nontrivial impact on propagation velocity. The study further concludes that " . . . In agreement with previous studies, we find that ephaptic coupling increases propagation velocity at low gap junctional conductivity while it decreases propagation at higher conductivities. We also find that conduction velocity is relatively insensitive to gap junctional coupling when sodium ion channels are located entirely on the cell ends and cleft space is small". As concluded by this and other clinical as well as etiological studies, the extracellular space and its extracellular potential φe 41 with its varying conductivities and capacitive values Cm relative to its intracellular potential 43 φ'$_i$, demonstrate that cellular structure and geometry has a nontrivial impact on propagation velocity.

The use of the sensor module 520 solves these and other problems by enabling the investigator in his electrophysiological study to identify the spatial location of the bioelectric potential by further accounting for the ephaptic effect of the conduction path with the MOSFET sensor's ability to mimic the potential via a variable resistor as well as a local amplifier and a ground potential set locally within the contact between the cell and the sensor surface. The use of the MOSFET sensor with its significant SNA ratio, greatly reduces noise and provides the signal fidelity necessary to emulate the ephaptic effects as noted by the above citation, that it has a nontrivial impact on propagation velocity. Complex arrhythmogenic causes cannot be accounted by the prior electrode technology due to the limitations as noted by the art.

Figure 2:
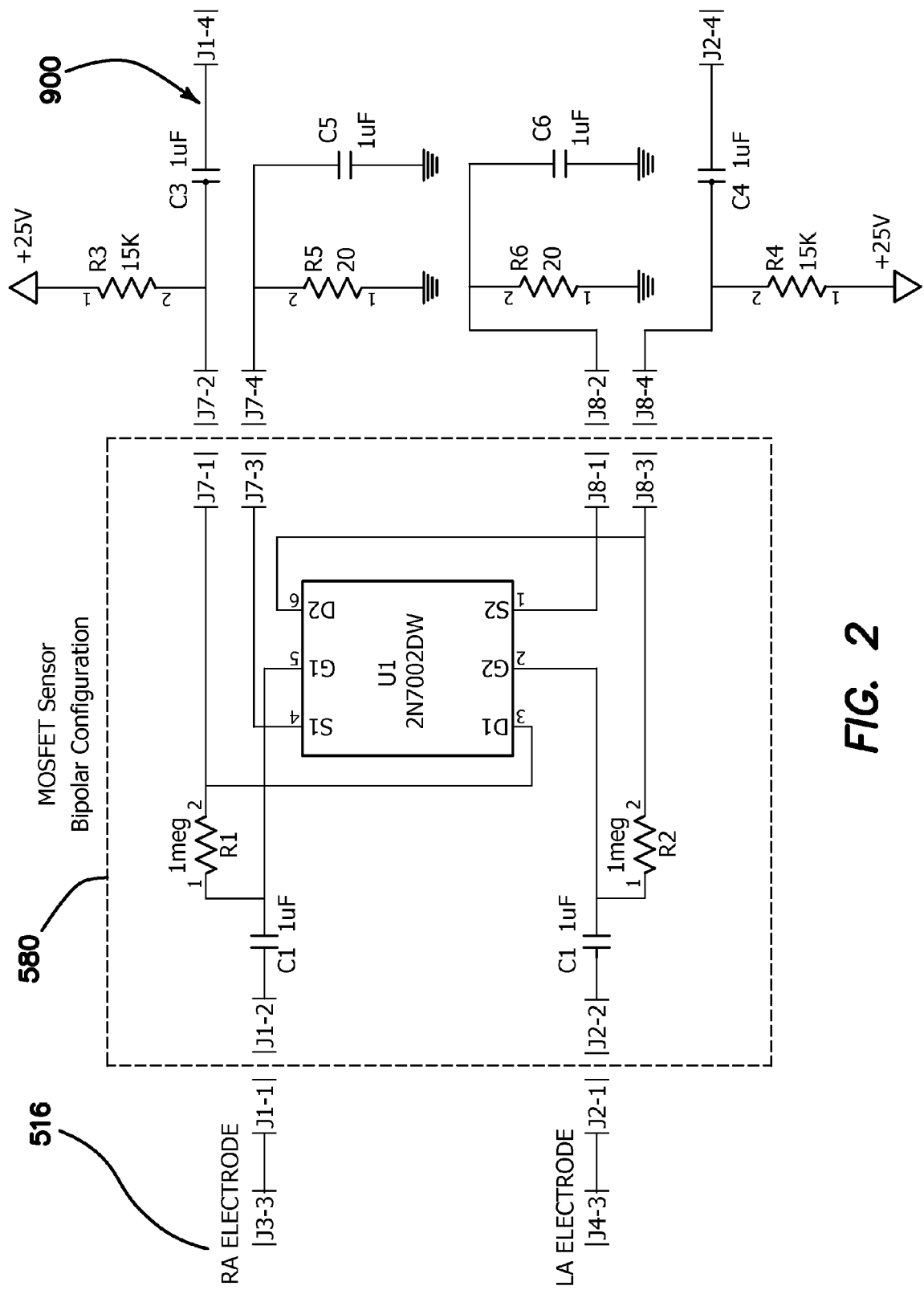
FIG. 2 is a circuit diagram of the embodiment of the MOSFET catheter with its associated circuitry.

FIG. 2 is a schematic representation of MOSFET output in its optional configuration as unipolar (not shown in FIG. 2) and bipolar differential output of the sensor configuration 580 circuitry the figure depicts the connections to the electrode ring 516 and further indicates the wiring arrangement to the power conditioning circuitry 900. The use of U1 2N7002DW, noted by the schematic can be substituted for optional configurations employing other MOSFET devices, such as MAX9638AVB single-supply CMOS input op amp, mfg by Maxim Integrated Products Inc. Sunnyvale, Calif.

Figure 2A:
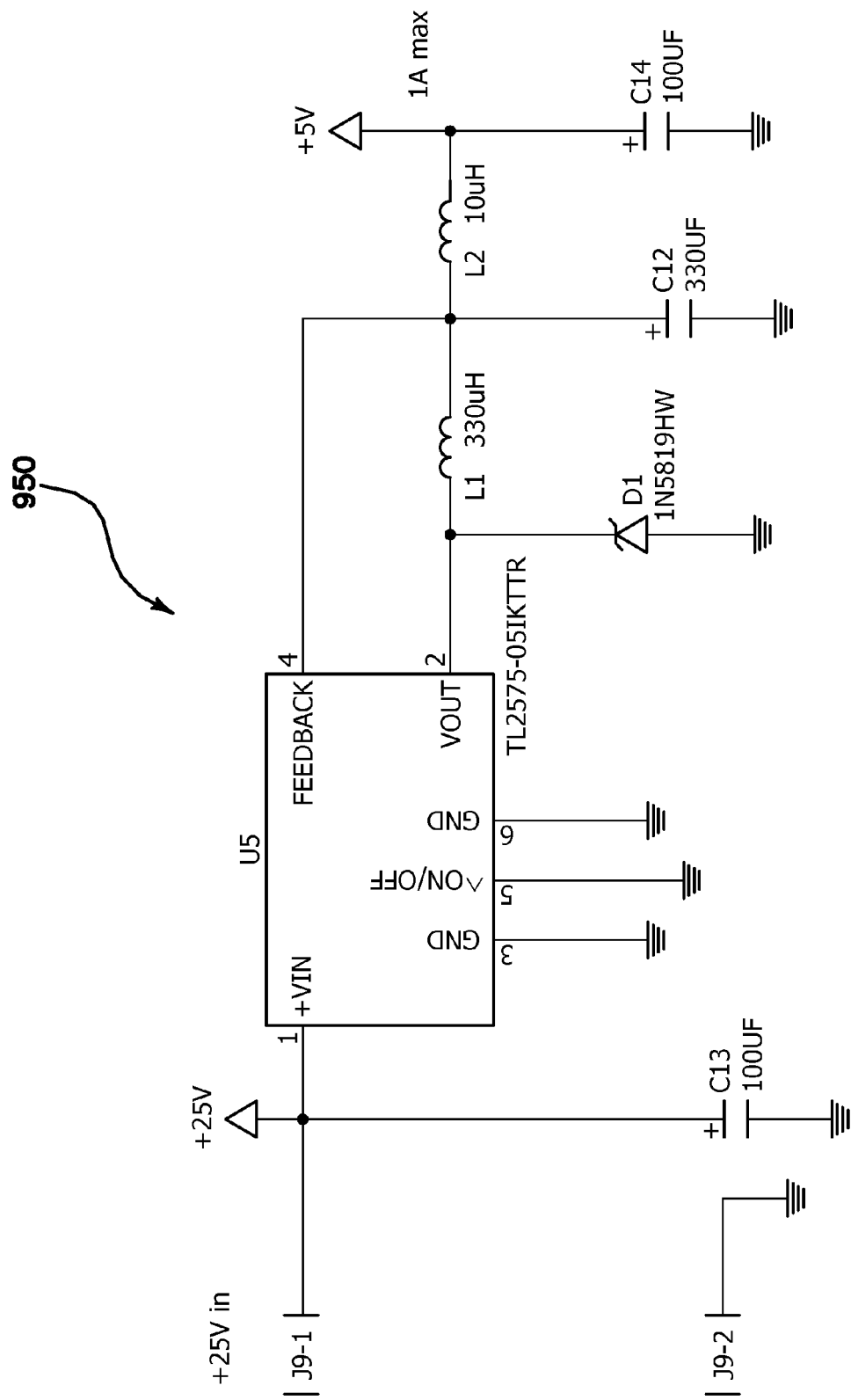
FIG. 2A is a circuit diagram of the embodiment of the power supply.

FIG. 2A is a schematic representation of the power supply 950 for the system apparatus 600 in an exemplary configuration using Texas Instruments TL2575-05IKTTR simple step-down switching voltage regulator to provide the necessary power conditioning circuitry for the EKG amplifier 960. A practitioner familiar with the art can conceive of many variations for such architecture to achieve the same function.

Figure 2B:
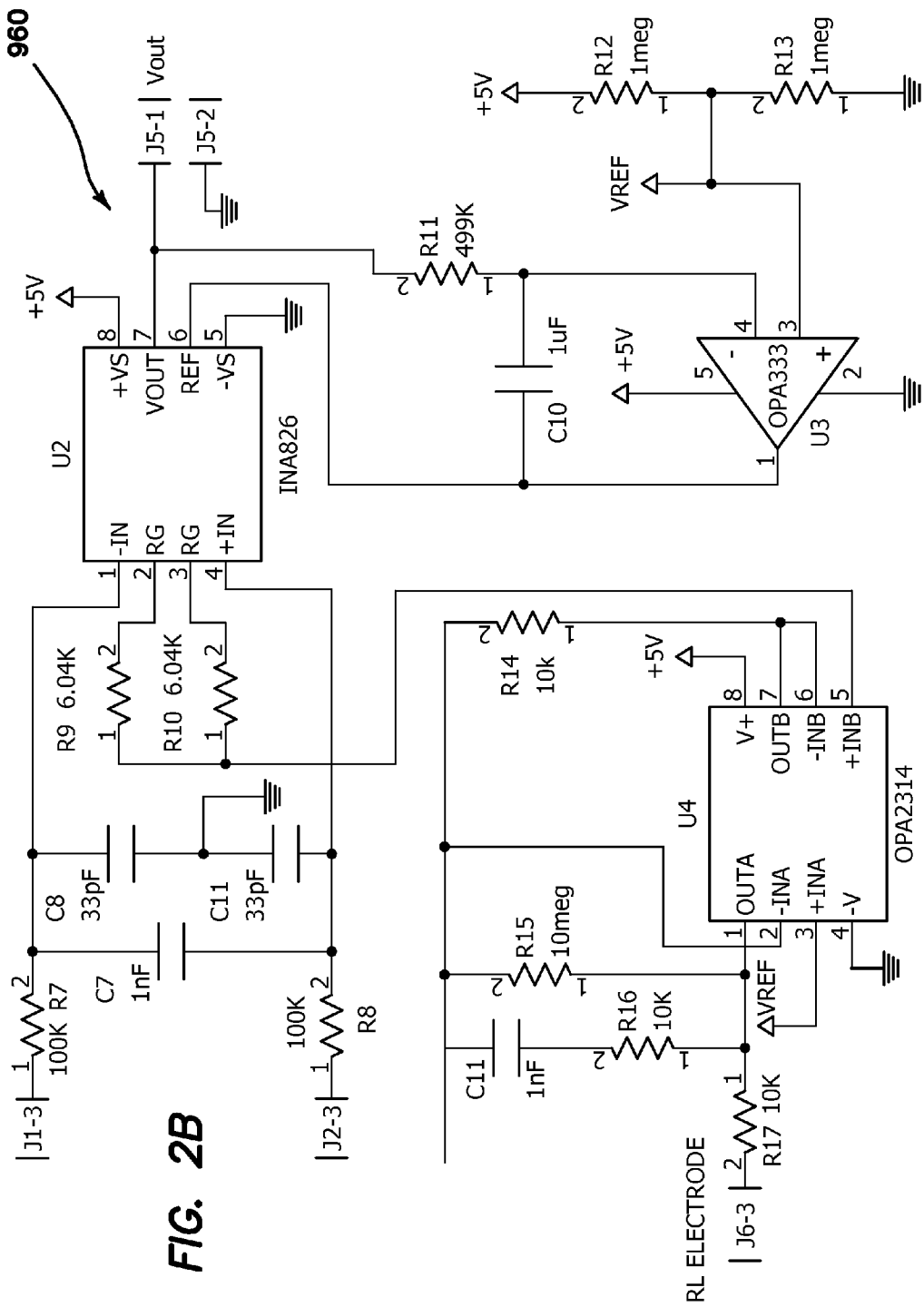
FIG. 2B is a circuit diagram of the embodiment of EKG amplifier employed by the MOSFET sensor.

FIG. 2B is a schematic representation of the EKG Amplifier 960 circuitry, in one embodiment where the amplifier is fitted with using a Texas Instruments OPA2314 CMOS operational amplifier, supply instrumentation amplifier, and precision zero drift CMOS operational amplifier. This architecture is an exemplary embodiment of the signal conditioning and amplification generated by the disclosed MOSFET sensor array 500, and a practitioner familiar with the art can conceive of many alternatives of substituting such an apparatus.

Figure 2C:
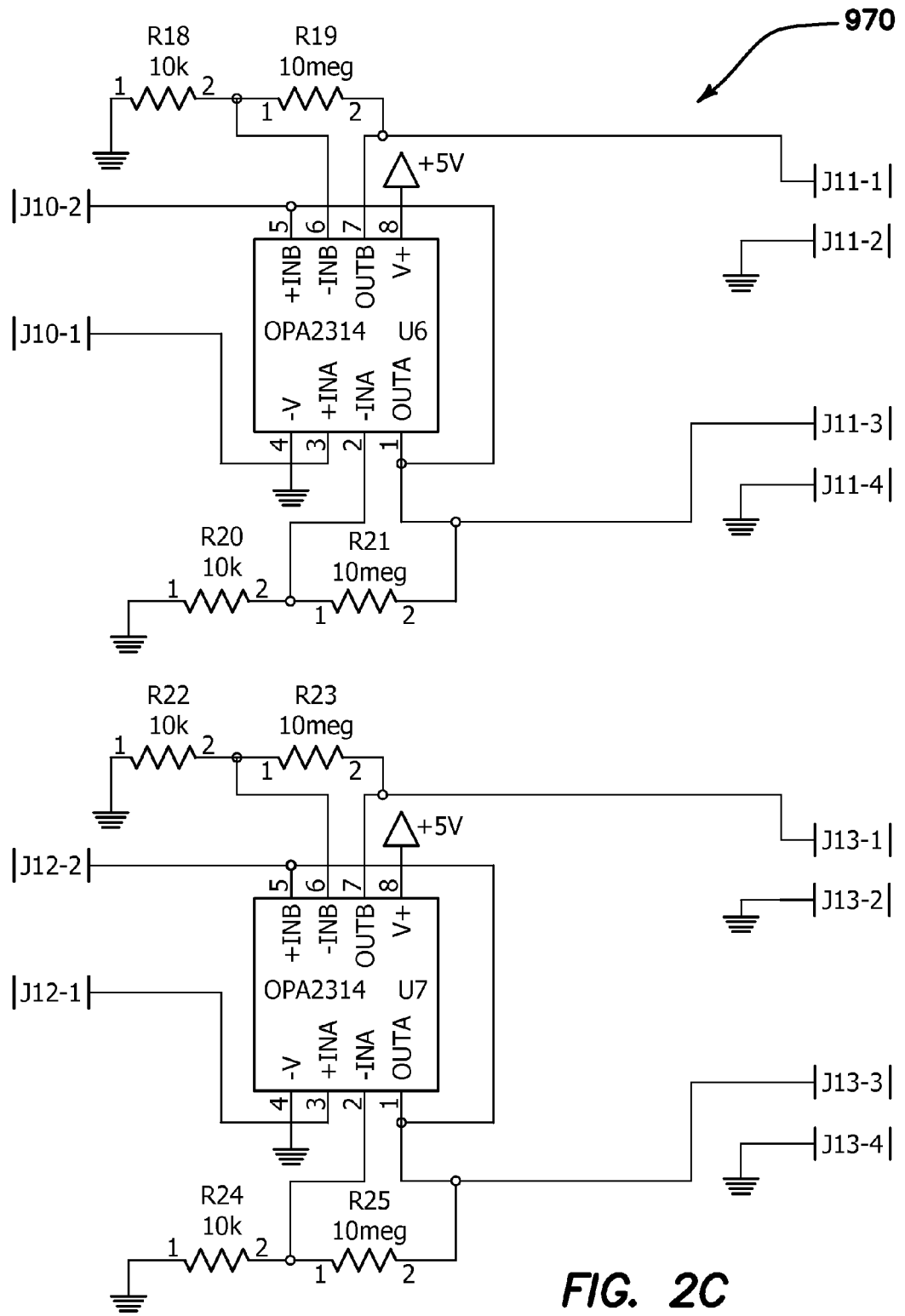
FIG. 2C is a circuit diagram of the MOSFET sensor in a bipolar scheme.

FIG. 2C is a schematic representation of the bipolar MOSFET sensor module low-power amplifier 970 with two channels providing unipolar and differential bipolar output. In one embodiment of the system 600, the disclosed MOSFET sensor array 500 is fitted with alternative architecture as an interface performing the signal conditioning and digital signal processing (DSP) functions.

Figure 2D:
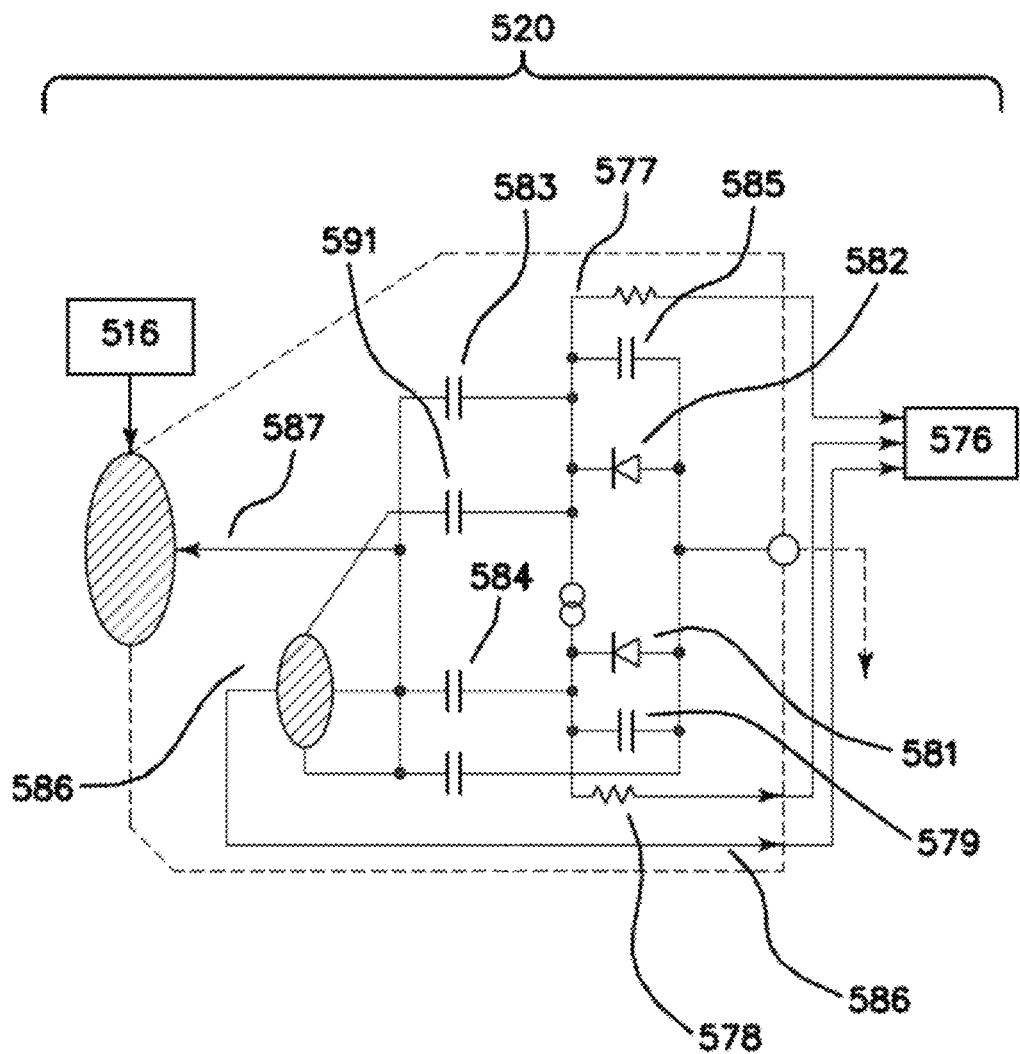
FIG. 2D is a circuit diagram of the internal equivalent circuit of the MOSFET module.

FIG. 2D is an orthographic depiction of the internal equivalent circuit of the sensor module 520 (an element of the MOSFET sensor array 500). In one embodiment a decapotar catheter with ten MOSFET sensors is fitted on the snapping catheter 800.

The MOSFET potential sensing device is a junction field effect transistor that allows a current to flow which is proportional to an electric field, basically emulating a voltage-controlled resistor. The sensor module 520 includes a resistor. The resistor RD 577 is a linear resistor that models the ohmic resistance of the source. The charge storage is modeled by two non-linear depletion layer capacitors, CGD 583 and CGS 584, and junction capacitors CBD 686, ID 591, and CBS 579. The P-N junctions between the gate and source and gate and drain terminals are modeled by two parasitic diodes VGD 582, and VGS 581. Gate #1 of the MOSFET sensor tip is item 587 and gate #2 of the sensor module 520 is item 586. Gate #1 with reference designator 587 at the electrode ring 516 is designated by (n)A (n=I, 2, 3, . . . 10) is a relatively high impedance, insulated semiconductor structure. The sensor module 520 behaves as voltage-controlled resistor. The potential between the gate structure 587, 586 and the drain source structure (RS 578, RD 577) semiconductor substrate defines the transconductance of the output connections 576.

By connecting the drain-source 577, 578 structure to the electrode ring 516 the potential reference for measurement is established. This reference is configured as an electrode ring 516 along with the catheter body 800 as shown in FIG. 1A. The measurement process of sensor module 520 is set to a zero voltage as the drain-source 577, 578 structure, the sensor's gate junction 587 assumes the tissue potential with a relatively small charging current flowing into the net parallel sum of the junction capacitors, CBD 585, CGD 583, and CGS 584. The drain-source 577, 578 voltages is then applied gradually to the device charging these capacitors from the outside power source, thereby "nulling" the current needed to form the gate so as to obtain the operating potential (about 6 VDC). The sensing procedure is relatively noninvasive to the cell as well as to the potential level and current drain of the sensor module 520 upon contact with biopotential of the tissue. Gate #2, item 586 provides a biasing input so as to provide a continuous active mode for the sensor module 520. This input is also used for self-calibration of the sensor module 520.

Figure 3:
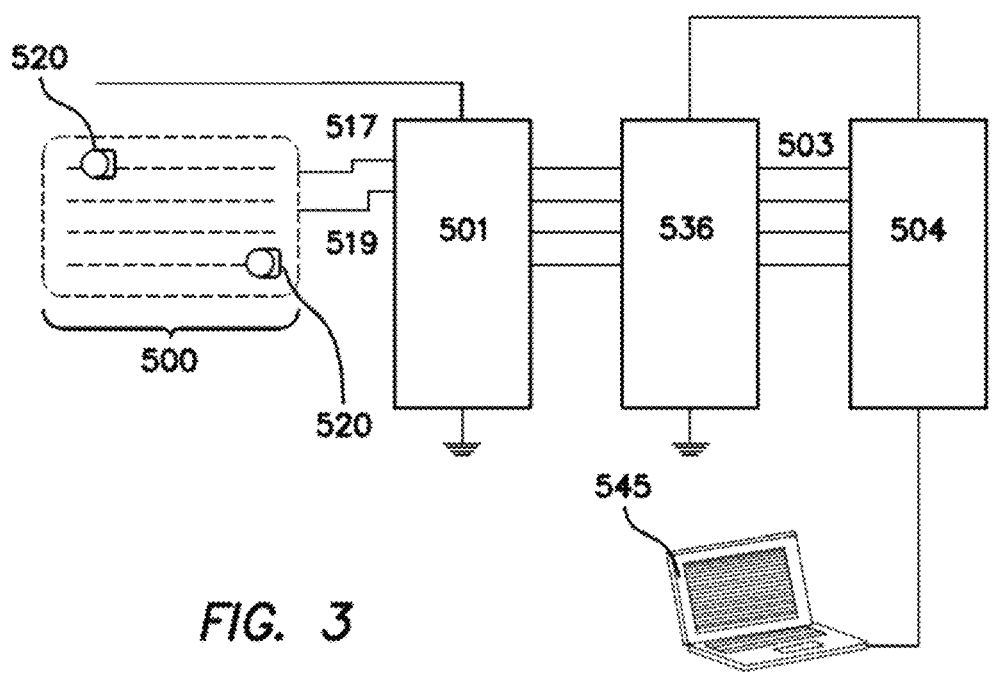
FIG. 3 is a system block diagram or a circuit for measuring and recording of the signals from the MOSFET sensor array.

FIG. 3 is an illustration of an embodiment of the apparatus 600 for measuring and predicting electrophysiological parameters associated with the use of the MOSFET sensor array 500. In one embodiment, the system apparatus 600 is employed in defining the proximity of the sensor array to the tissue surface and for measuring the bioelectric potential of the site. In another embodiment, the apparatus 600 is optionally fitted with pressure information relative to a correlated impedance values such as it is known in the art as "look-up tables", and as shall be evident from the theory and principle of operation of the sensor module 520. Data extracted by the catheter 800 on the surface of, for example, the artery inner lumen and/or endocardial surface further provides a measure of pressure generated while touching the arterial inner diameter of the artery by means of electrical properties such as dielectric and conductivity variation of arterial verses vein structure, similarly the apparatus 600 provides for a proximity impedance measure relative to the endocardial tissue. The principle articulated by this application provides for a measure of differentiation between blood pull impedance verses excitable cells or alternatively by measuring the nerve ending impulse in ganglionic plexus. In one embodiment, the conductivity (σ) measured in S/m and dielectric of the tissue (κ) at the site of measurements providing a measure of relative impedance which can be addressable by the look-up tables.

In one embodiment of the present invention the MOSFET sensor array 500 employ an integrated measure of contact as a measure of impedance value. The impedance measure derived from the MOSFET sensor array 500 produces analog voltage signals corresponding to biopotential, impedance measure, and temperature information by the MOSFET sensor array and its signal processor 530. The bioelectric potential signal output 518 is conveyed by the AC voltage at one of the outputs 517 of the measured biopotential due to pressure exerted between the sensor located at the distal end of the catheter 800, while the DC voltage of the third output 519 indicates if the catheter is in contact with the arterial structure or the catheter distal end is suspended within the lumen of the vascular inner diameter and/or the endocardial chamber blood pull. This measure is a function of the varying impedance values relative to the electrical properties of the vessel's dielectric, conductivity σ and relative permeability μ.

The basic relationship between the MOSFET sensor array 500 and the biological media while measuring impedance value is characterized by $$Z = \sqrt{\frac{j\omega\mu}{\sigma + j\omega z}},$$

where μ is the magnetic permeability, ∈ is the electric permittivity and σ is the electrical conductivity of the biological substrate, the wave travelling through the media is measured in the angular frequency of the wave ω. An example of such expression in free space is noted by $\mu=4\pi*10^{-7}$ H/m and $\in=8.854*10^{-12}$ F/m. So, the value of wave impedance in free space is approx.

$$Z \approx \frac{377}{\sqrt{\varepsilon_r}} \Omega,$$

the Z measure vary within the population, but it is clearly differentiated when measured while the sensor module 520 is in a suspended state as compared with its Z value when the MOSFET sensor array 500 of the catheter 800 is touching alongside of the artery or cardiac tissue. The Z value provides the MOSFET sensor array 500 with a clear measure of determining the sensor proximity to the arterial structure or its contact. This measure is used by this invention to facilitate a consistent application of the sensory apparatus during the mapping phase of the procedure when defining the exact location of the site i.e. depicting the biopotential value, amplitude, frequency etc. and by enabling an accurate account of the position measured, using such information, the operator is able to deliver the curative energy to effect the intended goal of neuro-modulation as well as remodeling of the electrical activity of an arrhythmogenic site within the cardiac chamber of the heart.

Figure 3A:
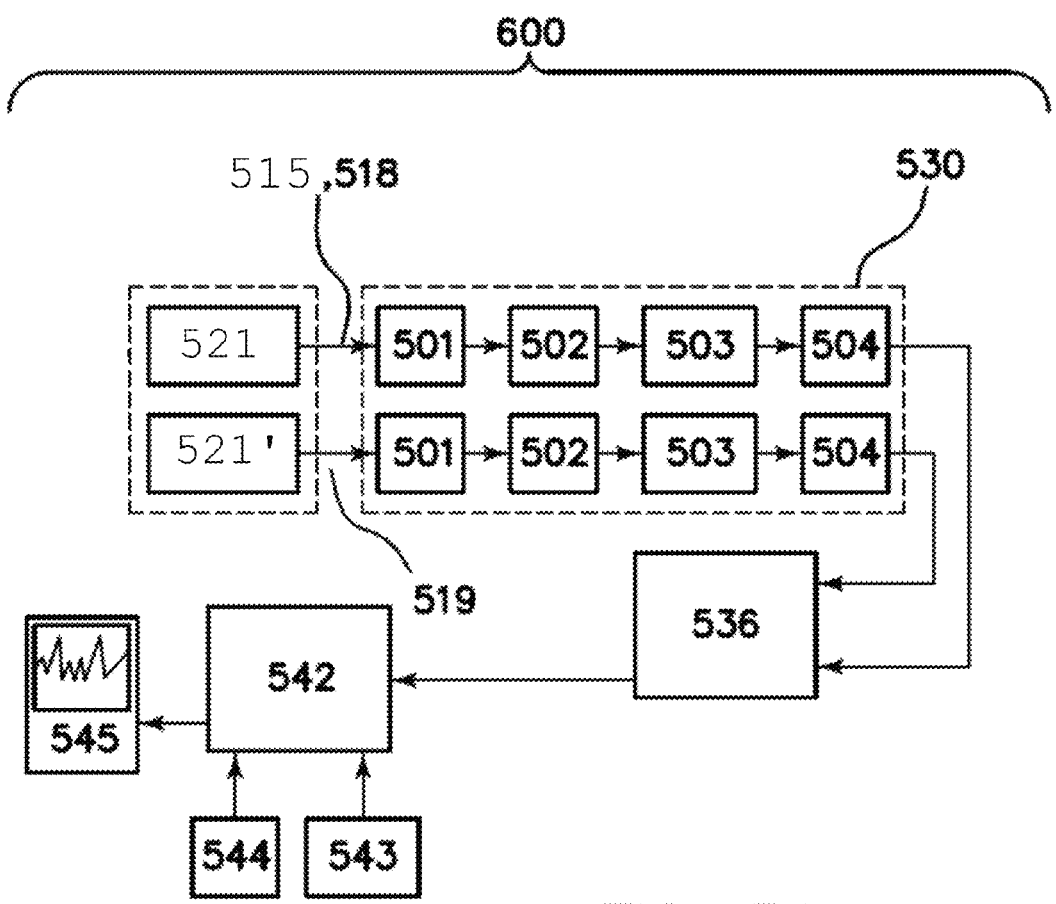
FIG. 3A is a system block diagram with multiple data collection channels.

FIG. 3A is an illustration of the system 600, block diagram of the triple signal processing modules. Each channel 521, 521' has three outputs. Output A 518 and output B 515 are the bioelectric potential and pressure signals respectively. The third output 519 is the temperature measurement signal. These outputs are analogue signals. Each of these signals is converted into 16 bit data packets of digitalized information via the ADC 501, which are serially transmitted to the microcontroller 536. The microcontroller coordinates the signal processing and display procedures. A computer console 542 with associated display 545, keyboard 543 and mouse 544 facilitates the monitoring and mapping procedures, as well as the alert system notification via the algorithm as well as parametric analysis. The signal analysis relay on the fidelity of the signal generated by the apparatus 600. Further analyses generated by the microcontroller 536. Or the host computer 542 is for example amplitude, mean frequency and or spectral density using a fast Fourier transform (FFT) method. In one embodiment of the system 600, the disclosed MOSFET sensor array 500 is fitted with alternative architecture as an interface performing the signal conditioning and digital signal processing functions. The device, RHA1016, mfg by Intan Technologies, LLC of Salt Lake City, Utah, is an integrated, low-power amplifier array containing 16 fully-differential amplifiers with programmable bandwidths suitable for use by system 600 while incorporating the signal generated by the sensor module 520 and by further providing bioinstrumentation monitoring and recording capabilities.

Figure 4:
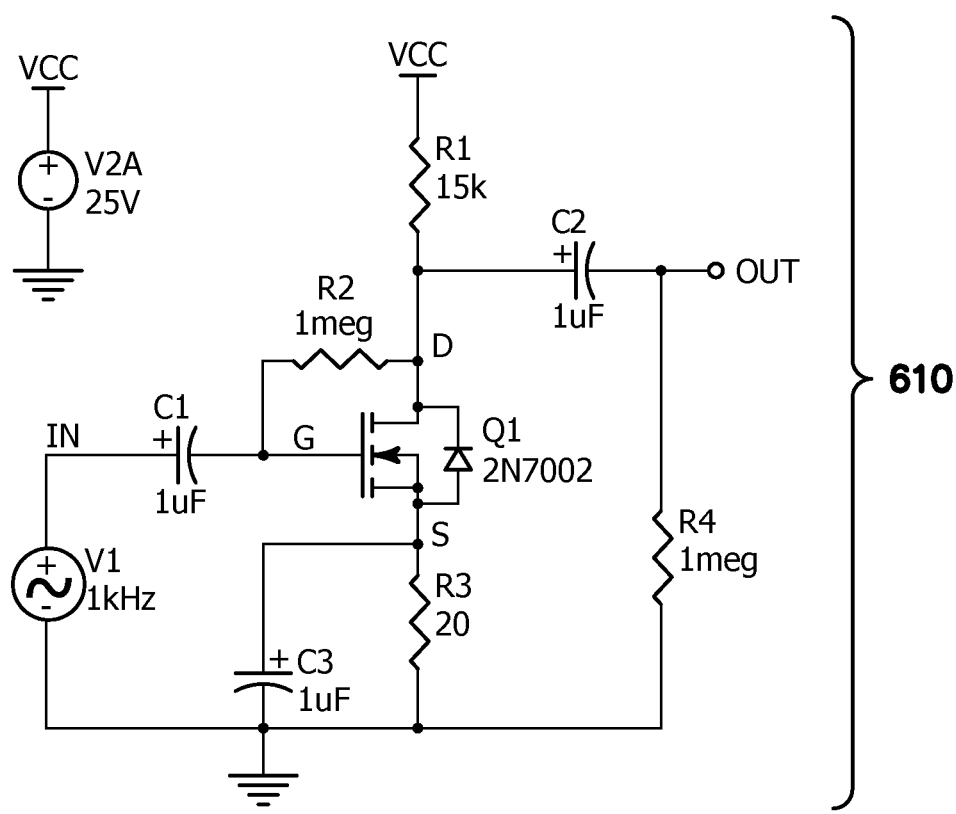
FIG. 4 is a circuit schematic of a simulation layout circuit describing the basic electrical characteristics of the MOSFET sensor module.

FIG. 4 is a schematic representation of a simulation layout circuit 610 describing the basic electrical characteristics of the sensor module 520, whereby the sensor module was excited with a 1 kHz using function generator (V1) and whereby the output was measured as shown in the embodiment and specification. The figure further describes a MOSFET common-source amplifier in SPICE simulation, R2 between the gate (G) and drain (D) terminals of the MOSFET biases the transistor in active mode. R3 and C3 between the source (S) and ground improves and stabilizes the small-signal gain of the circuit, C1 and C2 isolate the DC signal and ensures the small-signal (AC) amplification of the MOSFET circuit. The simulation indicates the ability of the circuit to vary the gain on the transistor (Q1 2N7002, N-channel enhancement mode field effect transistor) by varying the capacitance (C1) and its effect on the gain (G) of the transistor (Q1).

A practitioner familiar with the art can conceive of multiple other uses of similar MOSFET gates to perform the function as noted by this application. The elements disclosed by this application enhance the ability of the sensor module 520 to measure bioelectric potential at a site with fidelity and accuracy, including spatio-temporal representation of the local activity without the acquisition of "far field" and "near field" averages.

Figure 5:
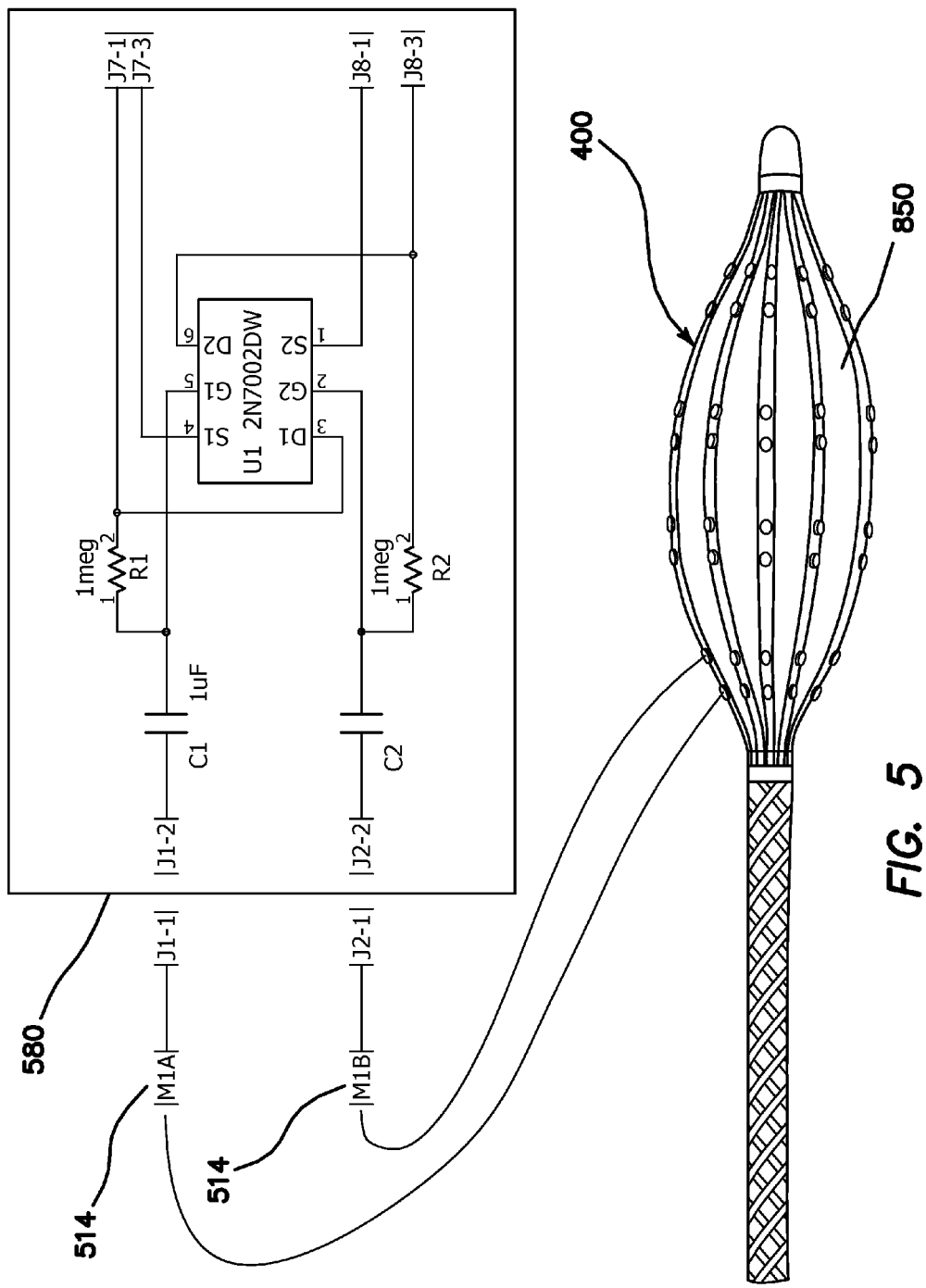
FIG. 5 is perspective diagram of the decapolar MOSFET catheter with an inflatable balloon and a corresponding circuit that can be employed to generate an electro-anatomical map in a body tissue.

FIG. 5 is diagram of the 8×8 matrix electrode array 400 MOSFET fitted on a catheter with an inflatable balloon that can be employed to generate an electro-anatomical map in a cardiac tissue. The mapping catheter is comprised of an open lumen catheter shaft 800 with a collapsible, basket shaped distal end 850 fitted with electrode pads 514 connected to MOSFET sensor configuration 580. Currently basket catheters include eight equidistant metallic arms, providing a total of 64 unipolar or 32 bipolar electrodes capable of simultaneously recording electrograms from a cardiac chamber. The catheters are constructed of a superelastic material to allow passive deployment of the array catheter and optimize endocardial contact. The size of the basket catheter used depends on the dimensions of the chamber to be mapped, requiring antecedent evaluation (usually by echocardiogram) to ensure proper size selection. The collapsed catheters are introduced percutaneously into the appropriate chamber where they are expanded.

Figure 5A:
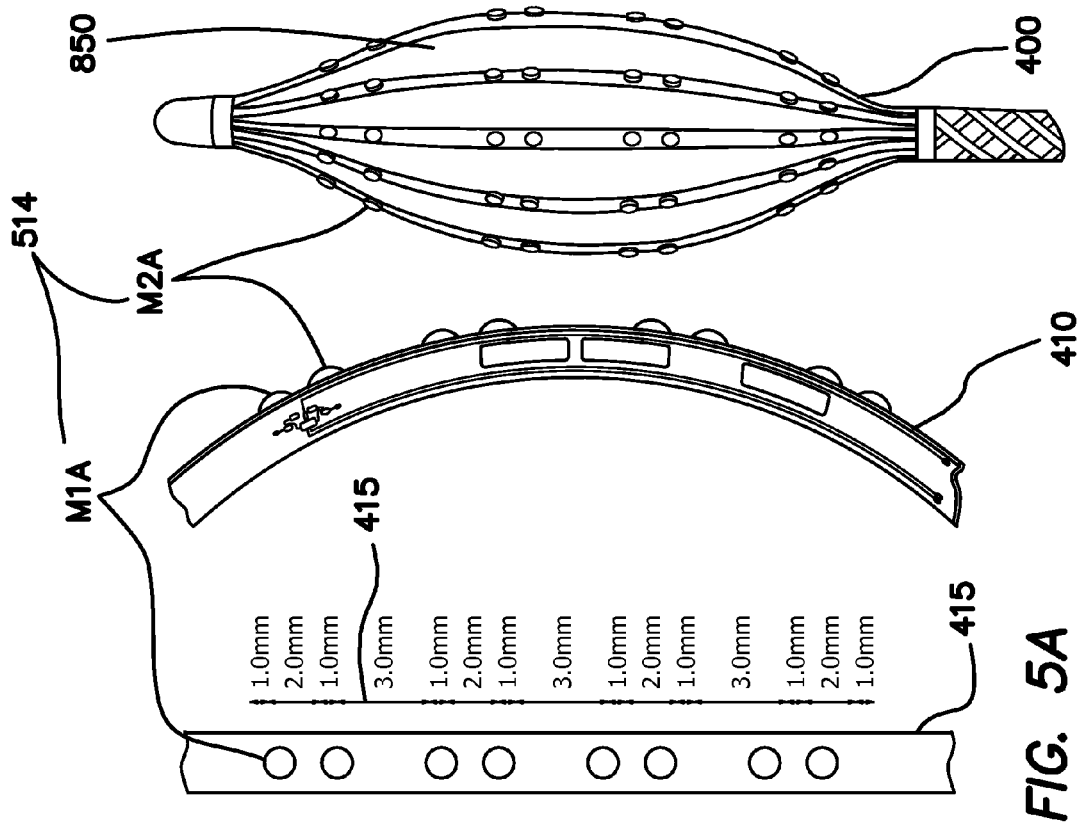
FIG. 5A are diagrams of the embodiment of the MOSFET sensor elements formed over a balloon with a corresponding circuit.
Figure 5A:
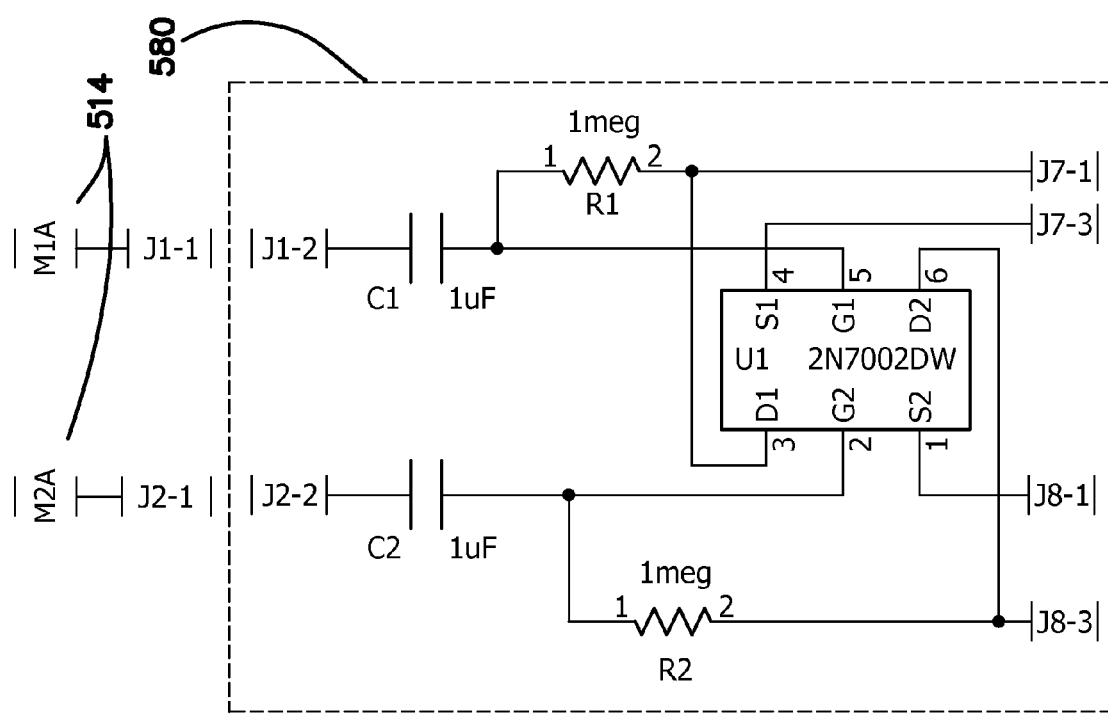

FIG. 5A illustrates an octopolar MOSFET spline array 410 with the electrode pads 514 as part of a bipolar MOSFET Sensor configuration 580, situated on the surface of a balloon catheter structure 850 in an 8×8 matrix electrode array 400 comprising of 64 MOSFET sensor nodes. The dimensional scale 415 of the array is utilized as a demonstration of the embodiment, but many optional spacing and array configurations can be formed based on the application and use.

Figure 5B:
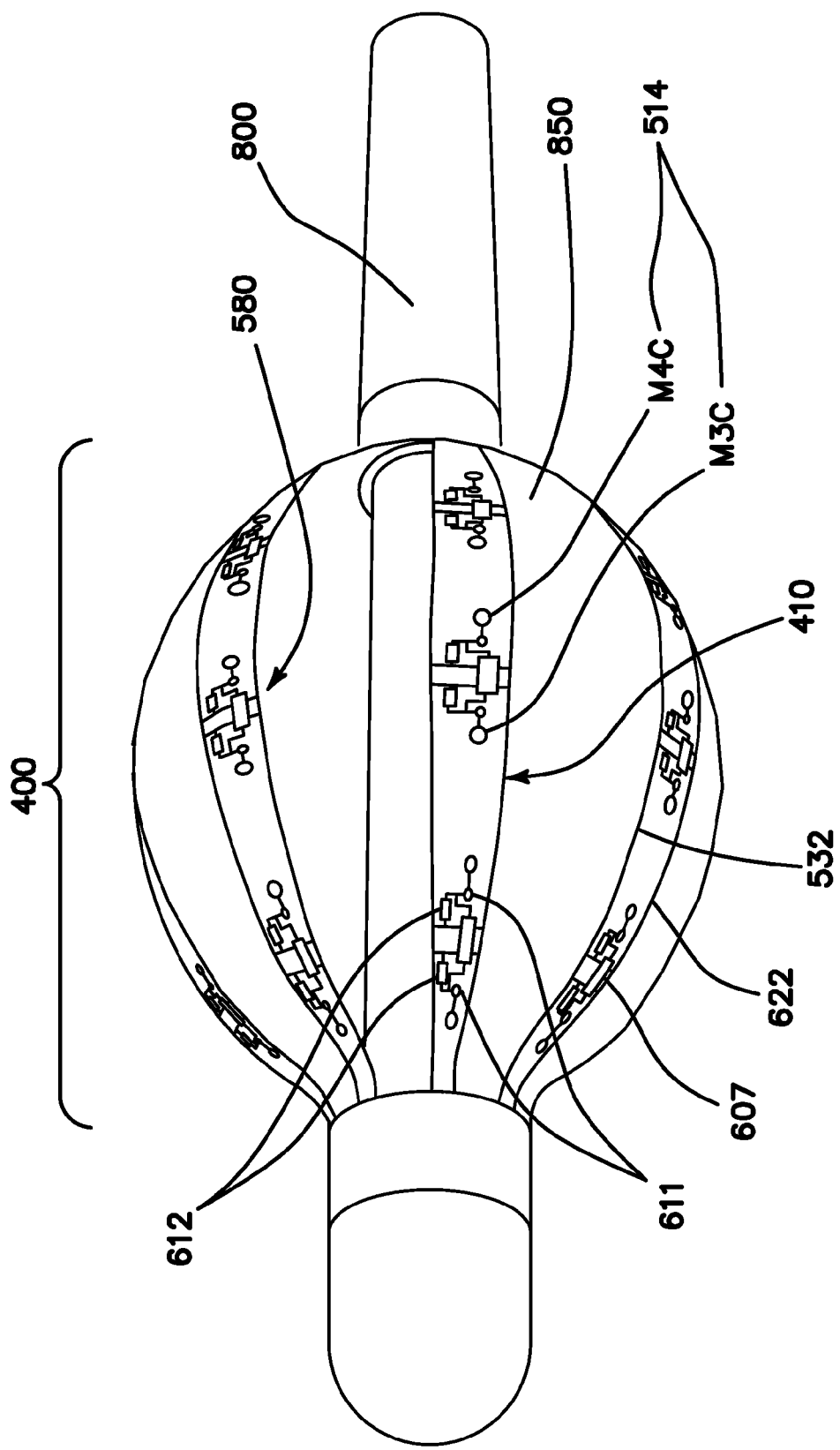
FIG. 5B is perspective view of the embodiment of the 8×8-Polar MOSFET sensor array formed over an inflated balloon catheter.

FIG. 5B is a diagram of an inflated balloon 850 on the catheter structure 800 fitted with a typical 8×8 matrix electrode array 400 formed of eight separate octopolar MOSFET spline arrays 410 in an octopolar arrangement of four individual bipolar MOSFET Sensor configurations 580 include the MOSFET 607 with its capacitors 611 and resistors 612, connected locally to their electrode pads 514 and externally by an output 622 and ground leads 532.

Figure 5C:
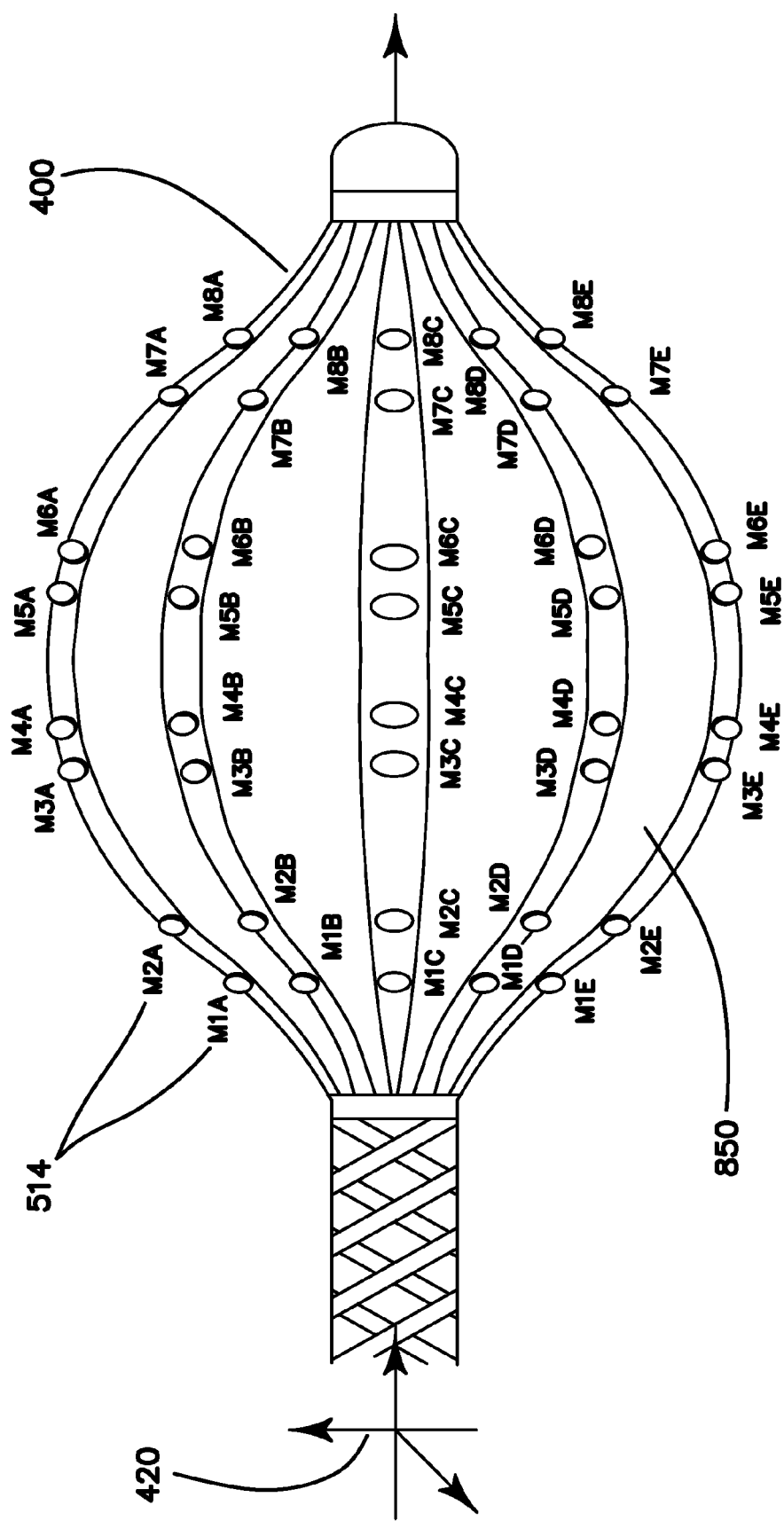
FIG. 5C is perspective view of the MOSFET sensor nodes and their relative position.

FIG. 5C is an autographic representation detailing a catheter structure 800 with balloon 850 formed with an 8×8 matrix electrode array 400 with the discrete indexing of electrode pads M1A, M2A, etc. 514 correlated to the sensor array orientation 420 extrapolated from the sensor output. The indexing of the array is logically connected to the auxiliary DSP and power units so as to enable measurement relative to orientation of the catheter spline proximal to the tissue surface as defined by the vector orientation 420.

FIG. 5D shows a schematic of an 8×8 matrix electrode array 400 for balloon catheter 850 such as described in FIG. 5 above, with a detail of a typical octopolar MOSFET spline marked as A 410 which is repeated on splines B-H, symmetrically distributed around the balloon surface and running lengthwise from the base of the balloon to the distal tip. The MOSFET spline array 410 is in further detail described by a sensor module 520 with its associated paired electrode pads M1A 514 and connecting capacitors 611, resistors 612 and MOSFET Q1A 607, governed by the external power conditioning circuitry 900.

Figure 5E:
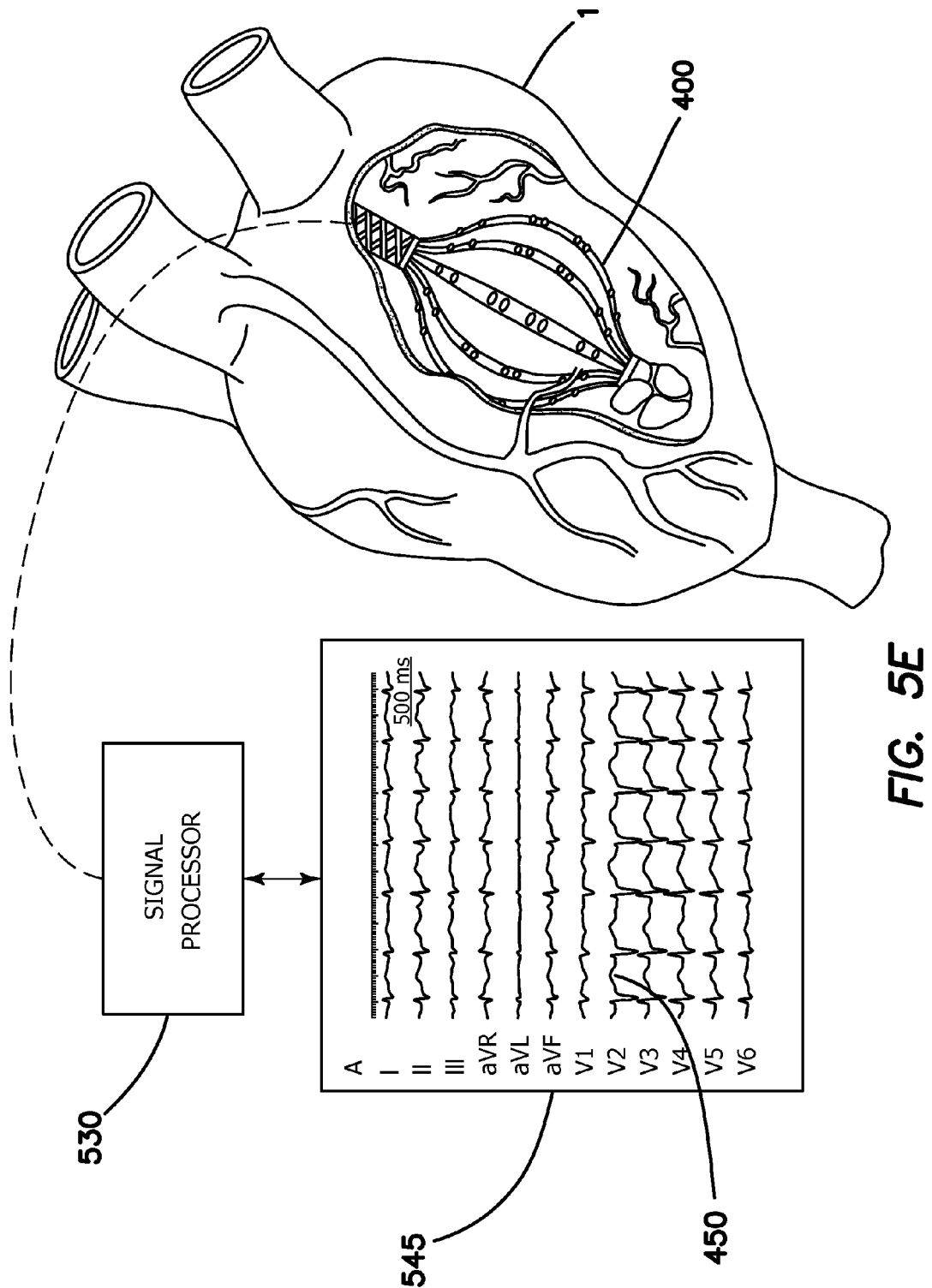
FIG. 5E is a perspective diagram of the catheter employed in a heart while being used to characterize the body tissue and in the left portion of the figure a graphical representation of the detected cardio signals.

FIG. 5E is a depiction of an atrial mapping procedure by balloon catheter fitted with an 8×8 matrix electrode array 400 inside the chamber volume of the heart 1, and the resulting output signal passed through a digital signal processor (DSP) 530 to a display 545 permitting real-time monitoring of the EKG waveform output 450.

The mapping system includes an signal processor 530 connected to a computer, which is capable of simultaneously processing: (1) 32 bipolar electrograms from the basket catheter; (2) 16 bipolar/unipolar electrograms signals; (3) a 12 lead ECG; and (4) a pressure signal. Color coded activation maps are reconstructed on-line. The electrograms and activation maps are displayed on a computer monitor 545 and the acquired signals can be stored on optical disk for off-line analysis. Activation marks are generated automatically with either a peak or slope (dV/dt) algorithm, and the activation times are then edited manually as needed.

The multi-electrode endocardial mapping system 600 shown in FIG. 3A allows simultaneous recording of electrical activation from multiple sites, and fast reconstruction of endocardial activation maps. This may limit the time endured in tachycardia compared to single point mapping techniques, without the insertion of multiple electrodes and facilitate endocardial mapping of hemodynamically unstable tachycardias.

With this system 600, a mapping catheter with tip and matrix electrode array 400 to record unipolar and bipolar signals is advanced percutaneously to the chamber of interest. The mapping procedure involves positioning the mapping catheter at sequential points along the endocardium. Catheter tip location and electrograms are simultaneously acquiring while the catheter remains in stable contact with endocardium. Local activation times are calculated relative to the body surface ECG or a fixed (reference) intracardiac electrode. The balloon catheter 850 fitted with disclosed MOSFET sensor array can be interfaced with existing mapping and processing apparatus, such as EnSite of St. Jude Medical, Minneapolis, Minn. and/or Carto Mfg by J&J BioSense Webster. A description of such data capture analysis and display are known to those familiar with the art of electrophysiology. Such a system continuously monitors the quality of catheter-tissue contact and local activation time stability to ensure validity and reproducibility of each local measurement. The acquired information is then color-coded and displayed. As each new site is acquired, the reconstruction is updated in real time to progressively create three-dimensional chamber geometry color-encoded with activation time. In addition to activation time maps, dynamic propagation maps displayed as movies of sequential activation on the computer workstation can be created. Additionally, the collected data can be displayed as voltage maps depicting the magnitude of the local peak voltage in a three dimensional model. These can be useful to define areas of scarring and electrically diseased tissue.

Mapping's high density parallel data acquisition yields high resolution maps of the entire cardiac chamber from a single beat of tachycardia, enabling registration of transient or hypotensive arrhythmias. Other useful features include radiation-free catheter navigation, re-visitation of points of interest, and cataloging ablation points on the three dimensional model. Mapping with high density parallel data acquisition employing the disclosed matrix electrode array 400 yields high resolution maps of the entire cardiac chamber from a single beat of tachycardia, enabling registration of transient or hypotensive arrhythmias.

The figure further illustrates additional detail of the example MOSFET 607. In this particular example, the electrodes are disposed on multiple splines, four of which are visible, and the splines are shown at an example treatment site inside a body cavity (e.g., the atrium shown in a partial cutaway view inside a patient's heart).

The distal inflatable balloon portion 850 includes a number of MOSFET sensors 607 on its expandable surface that can be employed to electrically characterize tissue that is contact with the electrode pads 514 at the treatment site. In particular, for example, the electrodes can be configured to support a detailed intracardiac electrophysiology study. Other types of electrodes or sensors can also be included on or near the surface of the balloon, such as, for example, thermal or pressure sensors.

The signal processor 530 electrically characterizes body tissue that is in contact with the sensor module 520. In particular, the signal processor 530 generates visual displays, such as isochronal or isopotential maps of the tissue, enabling a physician to identify aberrant electrical pathways at locations in the body tissue that are candidates for ablation. The visual display 545 provides the necessary graphical representations of the EKG waveform output 450 for analysis. In some implementations, the preferred embodiment may include a pressure sensor inside the balloon 850. In another embodiment, the balloon catheter 850 can carry a temperature sensor inside the balloon structure. Many variations on the theme of additional sensory output are conceivable for a practitioner familiar with the art, and can incorporate such diverse sensory output as temperature, pressure, pH, flow rate, capacitive and resistive measurements, to form additional data channels in support of the clinical needs associated with the formation of an electroanatomical map.

Figure 5F:
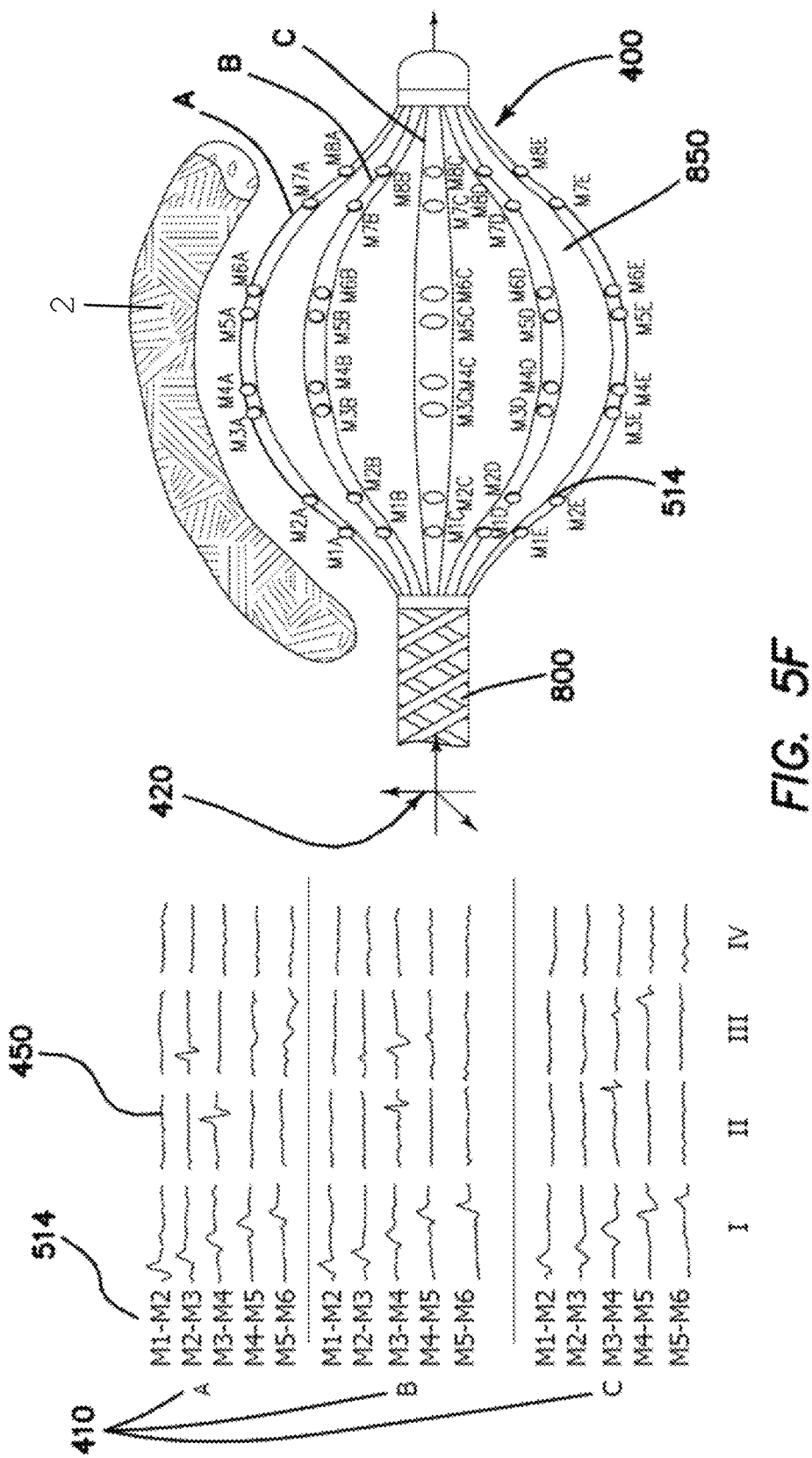
FIG. 5F is a perspective diagram of the MOSFET array catheter of FIG. 5 and in the left portion of the figure a graph of the electrical signal which can be obtained from the array.

FIG. 5F includes a chart illustrating the spatial-temporal corroboration between EKG waveform output 450 from sequentially-ordered pairs of electrode pads 514 along the length of the octopolar MOSFET spline arrays A, B, C, . . . H 410 with their placement around the circumference of a balloon catheter 850, generating the EKG waveform output 450 (noted by the chart) used to create the bioelectrical potential and activation map. The balloon catheter 850 with its matrix electrode array 400 is shown adjacent to an orthographic cross-section of the cardial tissue 2. The chart depicts the electrode pads 514 to detect an electrical signal designated "I" that propagates in this example parallel to the length of the pulmonary vein (and along the longitudinal axis of the splines). The chart illustrates an electrical signal is initially detected by MOSFET sensors M1 and M2 on splines A, B and C at nearly the same time. The time domain is represented by the x-axis of the vector orientation 420, the signal is detected subsequently at MOSFET sensor pair M2-M3, then pair M3-M4, then at pair M4-M5, then at pair M5-M6. Information about electrical signals, such as here shown, can be displayed in the user interface 545. In some implementations, the electrical characterization information includes static screen captures of biopotential information at different points in a particular region of body tissue. Points corresponding to electrode pads 514 on the inflatable balloon 850 provide information which includes customary description available from such systems known commercially as St. Jude Medical ENSITE or CARTO by J&J BioSense Webster, enabling a catheter to locate a target within anatomical context and by providing geometrical coordinates of specific anatomical destination. In addition, animations illustrating time-varying biopotential information includes color-coded isochronal or isopotential data; the graphic display can incorporate other information previously or contemporaneously obtained with other equipment. The figure further illustrates electrical signal designated by "II" that propagates along the circumference of the pulmonary vein and in a direction transverse to the splines, relative to the X axis of the vector orientation 420. In this example, the electrical signal II is first detected by MOSFET sensor pair M3-M4 on spline A, then on electrode pair M3-M4 on spline B, then on electrode pair M3-M4 on spline C. Another example, designated by reference "III" indicates the EKG waveform output 450 propagating both circumferentially and longitudinally along the cardial tissue 2. The electrical signal is first detected primarily by MOSFET sensor pair M2-M3 of spline A and secondarily by MOSFET sensor pair M2-M3 of spline B. Next, it is detected by the MOSFET sensor pair M3-M4 of spline B, followed by MOSFET sensor pair M4-M5 of spline B. Finally, the signal is detected by MOSFET sensor pair M4-M5 of spline C.

A final example, reference designator "IV", is provided in which no substantial electrical activity is detected at any MOSFET sensor pairs on any of the splines depicted. This example may correspond to a pulmonary vein that has been ablated to eliminate aberrant electrical signal sources or pathways that may be giving rise to or contributing to an adverse condition, such as atrial fibrillation.

Figure 6:
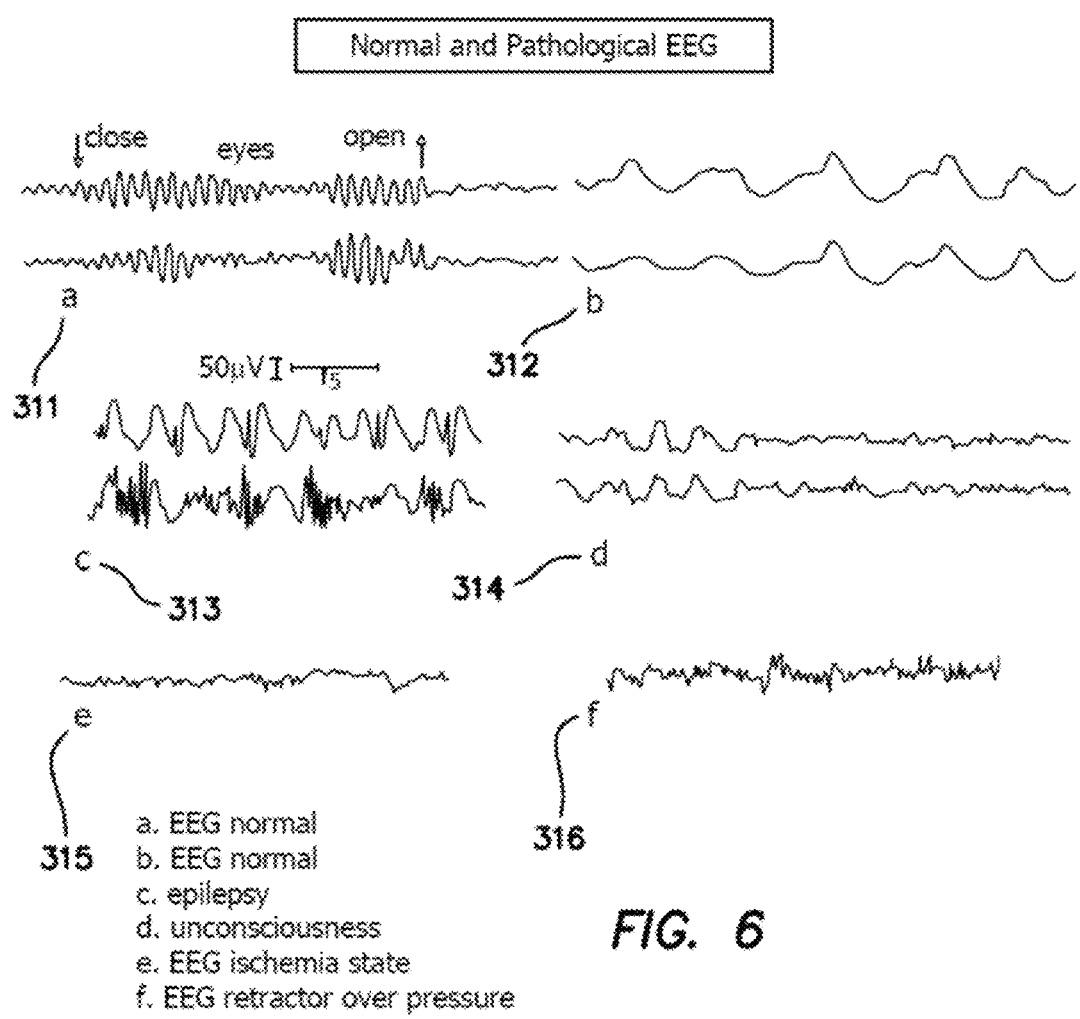
FIG. 6 is a graph of detected brain waves using an embodiment of the invention.

FIG. 6 is a graphical representation which depicts various brain waves typical of rhythms, powers or amplitude corresponding to occurrences which the presently described method is capable of identifying and isolating due to the ability of the sensor module 520 performance to sense a small biopotential value within the anatomical detail of brain electrical activity and by extension, to the SNA within the arterial structure of the renal artery or any ganglionic plexus. The MOSFET sensor array 500 described by this application is capable of collecting, sampling and measuring the power and amplitude of the signal generated, for example, by the renal artery plexus while dynamically traveling through the vascular tree. An example of such biopotential measurements are noted when comparing normal brain wave activities versus abnormal behavior associated with increased pressure or due to pathological inducement; Panel (a) 311 corresponds to normal (under no specific conditions) electroencephalogram brain wave readings. The leftmost signal corresponds to typical beta band waves when the person has his eyes closed. The center wave corresponds to the change in rhythm when the eyes are open, and so forth. Panel b, 312 suggests a similar wave pattern of a person under a different task, stereotypically of 'default mode' activity that could arise in the temporal or frontal lobes under EEG readings. Panel c, 313 corresponds to the same subject as panel b, 312 while the person is having an epileptic seizure. The rhythms become more pronounced, with rapid ripples and increased synchronicity on the envelope of the prior wave bands. In an embodiment of the presently described system employing the MOSFET sensor array 500, the system enables the physician to discern and identify these changes in power. Panel d, 314 is suggestive of an unconscious person's EEG reading. The decreased power, yet stable rhythm, is suggestive of a loss of consciousness. Panel e, 315 indicates the EEG reading of a lesion brain region, suggestive of the immediate effect of permanent pressure on the arterial structure or tissue, reflected by the MOSFET sensor array reading and is identified by the system 600. Panel f, 316 graphically represents the effect of over-pressure such as indicated by Mean Arterial Pressure minus the catheter surface with its MOSFET sensor array 500 pressure producing a state whereby the differential pressure is less than 70 mm Hg (<70 mm Hg) so as to further generate a typical wave reading as indicated. The use of the MOSFET sensor array in neuro surgical procedure, either for measuring synaptic firing, as well as brain or ganglionic electrical activity, is supported by the fact that any mechanical change exerted over the nerve ending will evoke a waveform characteristic that the MOSFET sensor array is capable of detecting, a further proof to the quality of measurement associated with the use of local measurement by a MOSFET sensor as we teach in this application. A patient undergoing pressure of 550 mm of water shows increased wave amplitudes in the MOSFET sensor array 500 reading, as well as short ripples suggestive of bursts of evoked potential in the area of where the catheter is exerting its pressure. Qualitative indications of the relationship between the etiological and mechanical state of the cellular structure under pressure and its electrical nerve activity are indicated by the use of the proposed disclosed technology. All of these cases are identified and isolated by the presently described system which further indicate the usefulness of employing a sensor with local amplifier and ground potential as exhibited by the use of MOSFET technology.

Employing the MOSFET sensor array 500 is contemplated when measuring sympathetic nervous system activity (SNA). The system 600 provides the physician (optionally using AI routines) with details of the electrical activity with a higher resolution on an order of magnitude beyond the prior electrode technology, as the MOSFET sensor module, exemplified by the apparatus described in this application, detects signal with a 0.1 µV sensitivity or less and with a 40-microsecond or higher sampling update rate (25 kHz). Such use of the sensor module 520 at the nerve ending of any ganglionic plexus provides signal fidelity and dynamic capture of the waveform or nerve impulse unmatched by the current electrode technology.

FIG. 6A is a graphical representation of a signal generated by a study using animals, which demonstrates the complexity of collecting bioelectrical potential signal data from ganglionic and nerve endings associated with the sympathetic nervous system (SNA). The ensuing figures, cited from Guild et al, in the study "Quantifying sympathetic nerve activity: problems, pitfalls, and the need for standardization," published in Experimental Physiology (95.1, pp. 41-50), details "the common ways of describing SNA . . . [Assessments of] the quality of SNA are made, including the use of arterial pressure wave-triggered averages and nasopharyngeal stimuli. Calculation of the zero level of the SNA signal from recordings during ganglionic blockade, the average level between bursts and the minimum of arterial pressure wave-triggered averages are compared and shown to be equivalent." The paper further recommends that the scale of measurement of neural and ganglionic activity in various plexuses must be set at the scale of microvolts and, as shown by the figures presented, the renal artery and the baroreceptor measurements represent a difference of ±10 µV with a resolution of ≥1.45 µV.

FIG. 6B is a graphic representation further elaborating on the observation that a recording of a short (2-second) example of renal SNA reveals that the integrated SNA 361, comprised of the original SNA 362 overlaid by the rectified original SNA signal indicated in the bottommost graph 367. As clearly exemplified by the figure, the use of electrode technology to identify the SNA signal and differentiate it from the ECG, electromagnetogram, and multiple electrical noises generated by various biological centers of body control, we must find the common mode rejection to enable the collection of high-fidelity ganglionic signal.

In another embodiment of the invention, it is clearly identified that a electrode pad 514 lying on the surface of a biological tissue is better suited to depict signal on the order of 1-5 µV without the distortion associated with the systolic wave emanating from the left ventricle during the cardiac cycle. The illustrated embodiment presented herein provides for local versus far-field signal, ground potential on-site (within the electrode pad 514), and fast-acting variable resistors based on MOSFET technology.

Figure 6C:
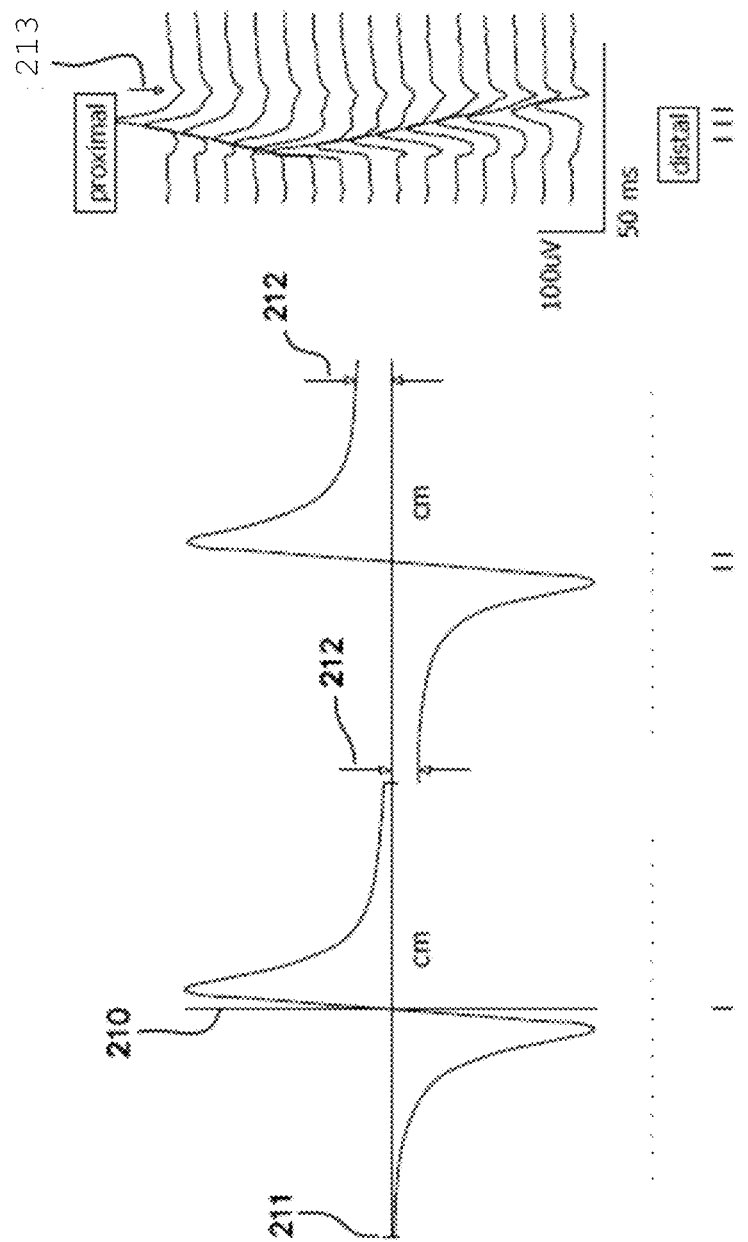
FIG. 6C are graphs of the difference between "far field" and "near field" waveform characterstics.

FIG. 6C is a graphic representation of the difference between "far field" and "near field" waveform characteristics. "Near field" and "far field" are distinguished as regions of bioelectrical emanation from localized anatomy, and from the surrounding corporal structures. Whereas a near-field potential waveform has clear changes in amplitude, polarity, wave shape and/or latency when the position of the active electrode is changed over a small distance, conversely, in the far-field the signal characteristics are not changed by moving the electrode position, hence the far-field signal component is a non-moving potential. In the seminal study by Cracco R Q et al, titled, "Somatosensory Evoked in Man: Far-field Potentials" Electroenceph Clin Neurophysiol 1976; 41:460-46, this phenomenon is represented in graph II as the non-vanishing portion of the decaying signal. The obvious background of such lack of waveform changes is the location of the electrode at a large distance from the bioelectrical source.

A fundamental aspect of clinical electrophysiology, the discipline of diagnosing and treating cardiac arrhythmias, is the interpretation of intracardiac electrical signals (electrograms), typically referred to as EGM's. All EGM's represent a voltage difference between two electrodes, whether the electrodes are in close proximity, i.e., bipolar EGM's, or at a relatively great distance (theoretically an infinite distance), i.e., unipolar EGM's. EGM's have traditionally been obtained as differential recordings formed between an anodal input to a distant amplifier versus a cathodal input to the amplifier. The EGM is thought to record local wavefronts of depolarization and repolarization, and typically assumes the viability of 1 to 2 cm$^3$ of myocardium under the recording electrode.

The unipolar EGM has an important role in the diagnosis of the origin of electrical impulses within the heart. By convention, the contact ("exploring") electrode is connected to the anodal input of the recording amplifier, hence in a uniformly conducting sheet of myocardium the approaching wavefront generates an upward deflection, which then becomes negative as the wavefront flows away from the recording electrode. An initial downward deflection is conventionally called a Q wave, whereas the upward signal is called an R wave, and the secondary negative signal (after the initial R) is labeled an S wave. For mapping purposes in the basic and clinical laboratories the maximum negative slope (−dV/dt) of the unipolar R/S signal coincides with the arrival of the wavefront directly under the recording electrode. When complex maps are generated by recording from many simultaneous unipolar and bipolar EGM's, this maximal negative slope of the R/S signal is calculated at each recording site and a propagation scheme is generated based on the spatial temporal differences between the different sampling sites. Possibly the single most important use of unipolar EGM's in the clinical laboratory is thought to be the use of specific morphologies of the recorded EGM. The morphology of the unipolar EGM is thought to indicate the direction of a wavefront propagation, such that when the exploring (anodal) electrode is at the site of initial wavefront activation, such as a focal tachycardia or an accessory pathway, a QS (all negative) signal is generated, as the depolarizing wavefront spreads away from this electrode. Theoretically, application of RF energy at a site manifesting a unipolar QS signal should prove to be successful ablation when the target arrhythmia is thought to be "focal" in nature. The reasons why this is not always the case are listed below.

Filtering of unipolar EGM's is typically performed using a corner frequency for the high pass filter of between 0.05 to 0.5 Hz. The high pass filter is needed to attenuate lower frequency baseline drifts caused by respiration, catheter movement and variable catheter-tissue contact. Higher corner frequencies for high pass filtering of unipolar EGM's are occasionally used when mapping ventricular scars, but it should be noted that filtering changes the morphology of the signal and renders it not useful as an indication of the direction of wavefront propagation, i.e. a QS signal generated by a filtered unipolar EGM cannot be used to infer a site of earliest activation.

A major disadvantage of unipolar recordings is that they contain significant amount of "far-field" signal, i.e., signals generated by depolarization of tissue remote from the recording electrode. As noted above, in normal, homogeneous tissue, the maximal negative slope is indicative of local depolarization occurring underneath the exploring electrode. In fibrotic or scarred tissue, small amounts of healthy tissue beneath the electrode may generate relatively smaller potentials than the surrounding myocardium, hence a large far-field signal can dwarf or obscure a small local potential. In addition, the size of an area generating a diagnostic QS at times exceed a centimeter and thus may be much larger than an arrhythmia producing focus. Thus, a unipolar QS signal is necessary, but not sufficient, in guiding a successful ablation of a 'local' tachycardia. It should also be remembered that a unipolar QS complex can be recorded when the exploring electrode is not in contact with the tissue, but, rather, may be floating some distance away within the cavity. Clinicians counter this problem when they recognize that the initial negative slope of the recorded QS signal is typically relatively slow when tissue contact is lacking, suggesting that the EGM is a far-field signal. This observation is quite subjective and often overlooked.

Bipolar EGM's are obtained by summing the potentials recorded form two adjacent electrodes which overlay the area of interest in the heart. The potential at the negative input is inverted, and thus subtracted from the positive input. In a homogeneous sheet of myocardium, the arrival of a depolarization wavefront coincides with the initial peak of the bipolar EGM. It is thought that bipolar EGM's are less prone to far-field distortion, hence they are primarily used to locate a point of earliest activation relative to a stable reference recording during a tachycardia or abnormal impulse formation. The signals are typically filtered using a high pass filter of 30 Hz and a low pass filter of 250 Hz. The 30 Hz corner frequency in this setting is thought to minimize far-field distortion and to preserve accuracy and timing of local activation.

Despite the theoretic considerations mentioned above, far-field signals are frequently recorded using relatively close bipolar recordings, i.e., 2.5 nm interelectrode distances. For example, EGM's from pulmonary vein ostia frequently manifest large "far field" atrial signals recorded from regions that are at the border between the atrium and pulmonary vein. Separating the signal of interest, i.e. pulmonary vein fiber potential (high frequency signal) from the "far-field" atrial signal (lower frequency, usually much larger signal) can sometimes be difficult, and requires pacing maneuvers and empiric RF energy application. In addition, differences in electrode sizes, for example large ablation distal electrode vs a smaller proximal electrode, might exaggerate the potential differences between the two electrodes and distort the resultant EGM signal amplitude, which is important for recording scar voltage. In addition, the direction of wavefront propagation influences the amplitude of the bipolar EGM (but not that of the unipolar EGM). Theoretically, a wavefront that, propagates in a direction that is exactly perpendicular to the axis of the recording dipole would produce no potential difference, hence no EGM signal. The clinical significance of this scenario in mapping scarred tissue is unknown, as these maps are dependent on displaying areas of "low voltage" as areas of scarred myocardium.

Existing intracardiac recording techniques, while they have served the clinician and basic scientist reasonably well over the past three to four decades, suffer from several inherent limitations, which this patent application seeks to address:

By their very nature, i.e., electrodes connected by long cables to a distant differential amplifier, these systems are subject to line "noise", ambient EMI, cable motion artifact, faulty connections.

Local signals, as described above, are subject to recording of "far field" signals, which at times render the interpretation of complex, rapid arrhythmias very difficult, if not impossible.

The conflation of "far field" and signals of real interest, such as pulmonary vein fiber potentials, accessory pathway signals, "slow pathway" potentials, can sometimes be the cause of failed ablations. The ability to record local electric activity with great precision and to the exclusion of "far field" signals would be of paramount importance.

Current recording systems frequently cannot differentiate low amplitude, high frequency signals from background noise. Extremely low amplitude signals, such as signals generated during slow conduction within a myocardial scar, are frequently missed or lost in the background noise when amplifier gain is made sufficiently high to attempt to record such signals.

Continuous, low amplitude, "fractionated" high frequency signals such as those frequently seen in the atria of patients with chronic atrial fibrillation, cannot be further characterized using existing recording technologies. These signals may contain important biologic and electrophysiologic information. For example, these signals may represent important areas of scarring that are responsible for formation of "rotors." Alternatively, they may be manifesting discharges from contiguous epicardial parasympathetic ganglionated plexi.

Graph I represents a near-field waveform characteristic, where the horizontal axis 211 denotes distance, and the vertical axis 210, the voltage. It is clear that the potential decreases monotonously with distance along the horizontal axis, therefore, the profile shown in graph II indicates the presence of additional far field source component 212 for the potential, as it is constant and non-vanishing, i.e.: representing the difference in potential between "far-field" and "near-field". This difference between the waveform relative to the horizontal axis 210, does not decrease over time, and can be subtracted by using the fast-acting local bipolar measurement available through the use of the disclosed MOSFET sensor array 500.

Graph III of FIG. 6C further indicates the fact that when unipolar measurements are made along the fiber directions of a muscle, the signal can be isolated from the surface EMG whereby the waveforms are composed of two main components, the propagating negative part (upward) in two directions, and the positive, non-propagating components, indicated by the arrow 213, which represent that the non-moving "far field" property is in the upper 9 traces, and "near field" characteristics in the lower 6 graces. This graph III represents the distinction between moving and non-moving components distribution of the far-field vs. the near-field.

Figure 7:
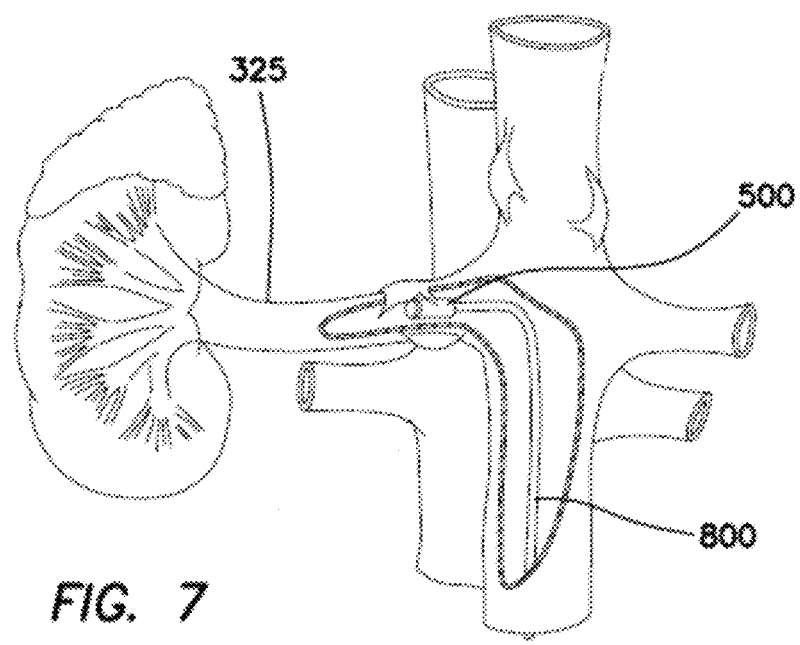
FIG. 7 is an illustration of the right renal anatomy which depicts a catheter fitted with a MOSFET sensor array being magnetically guided therein.
Figure 7A:
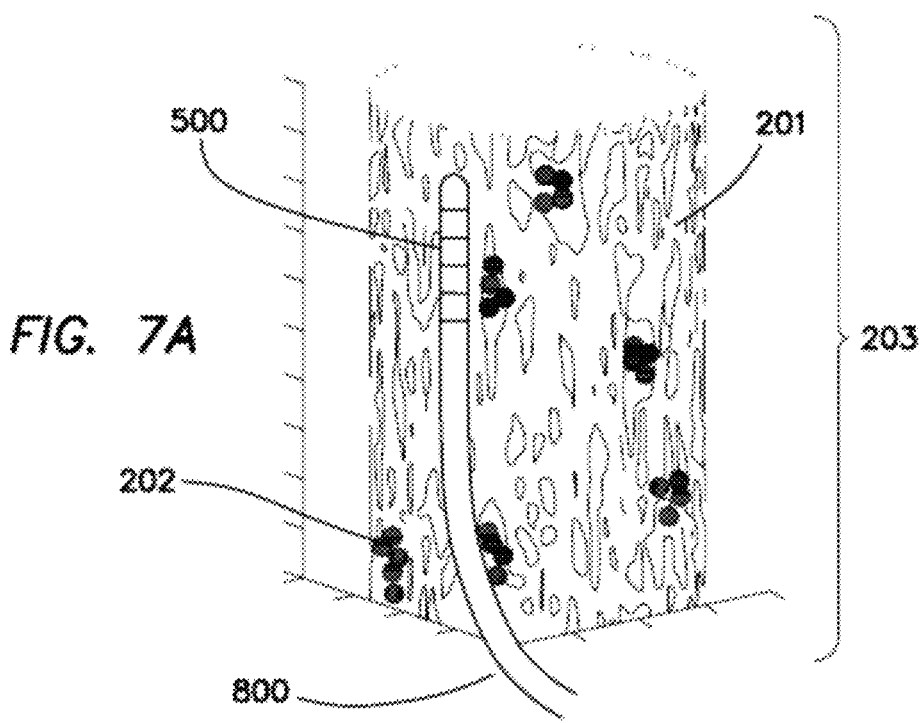
FIG. 7A is a perspective view of the renal artery detail and catheter tip.

FIGS. 7 and 7A are illustrations of the right kidney depicting anatomical details of the renal artery with its plexus, and a detail of a perspective view representing a renal artery signal map 203 containing both low level signal areas 201 and high level signal areas 202 as well as a visualization of the catheter 800. The cutaway of the renal artery further indicates the presence of a catheter 800 fitted with a MOSFET sensor array 500. The use of the disclosed apparatus 600 is demonstrated so as to enable an improved clinical procedure associated with the detection of the SNA emanating from the nerve ending. The common procedure for neuromodulation of the SNA on the renal artery plexus is a standard care currently employing the electrode technology to detect the location of the nerve ending within the adventitia structure.

In the ensuing paragraphs we highlight the fact that cellular etiology does provide us with electrophysiological indications, we further instruct in this application that the use of the apparatus proposed solves these and other problems associated with surgical ablation, and by the consistent application of the methods and embodiments of this invention a robust predictive outcome is enabled so as to dramatically reduce the incidence of morbidity associated with the use of mechanically translating and rotating catheter in the renal artery. While using a catheter to perform a neuromodulation by applying energy to block or redirect peripheral nerve impulse.

The figure further illustrates the incorporation of apparatus for facilitating remote magnetically guided delivery of a MOSFET mapping and ablation catheter 800 to innervated tissue and ganglia that contribute to renal sympathetic nerve activity in accordance with embodiments of the invention.

The standard method for neuromodulation associated with the curative approach to hypertension is to employ a mapping and ablation catheter to denervate the renal artery ganglionic plexus within the inner surface of the artery, proximal to the right or left kidney. In the standard care employed an RF ablation catheter is used cooperatively with an imaging system such as known the in art for example as St. Jude Medical ENSITE or magnetic localization system such as CARTO made by J&J BioSense Webster. This procedure of renal denervation, where a surgical intervention deactivates the ability of the sympathetic nerve or its ganglia to influence the activity of the sympathetic autonomic nervous system to further achieve a clinical outcome of reduction of hypertension is the mainstay of the existing art.

The disclosed MOSFET sensor array 500 will improve the clinical outcome by enabling the apparatus 600 with its catheter 800 to identify the position of high bioelectrical potential, by enabling the sensor module 520 to depict SNA emanating signal (from the renal ganglionic plexus) on the order of 1-5 µV, further providing a specific impedance value which indicates contact with the tissue. In one embodiment, the MOSFET sensor array is capable of at once reassuring a signal on the order of 0.1 µV, while contemporaneously measuring and indicating the proximity of the catheter 800 to the tissue, which is an additional improvement of the current invention.

The process described is governed by the use of the apparatus ability to first provide an indication of position and orientation of the catheter 800 with constant impedance value indicating surface contact with the vessel lumen so as to be enable to deliver the necessary RF energy through the adventitia and where the ablating energy is transmitted to the renal nerve and the ganglionic plexus in an optimal and safe mode.

In accordance with various embodiments described herein, one or more physiologic parameters can be monitored during the ablation procedure to determine the effect of the ablation on the patient's renal sympathetic nerve activity. For example, a matrix of MOSFET sensors is situated in contact with the inner or outer wall of the renal artery 325 near opposing sides of the renal artery.

In the ensuing paragraphs we highlight the fact that cellular etiology do provide us with electrophysiological indications, we further instruct in this application that the use of the apparatus proposed solve these and other problems associated with surgical ablation, and by the consistent application of the methods and embodiments of this invention a robust predictive outcome is enabled so as to significantly reduce the incidence of morbidity associated with the inability of the current electrode technology to detect nerve ending impulse in the orders of 0.1-10 µV. The use of the disclosed mapping technology will improve neuromodulation as an additional optional use of the proposed technology we teach in this application.

Figure 7B:
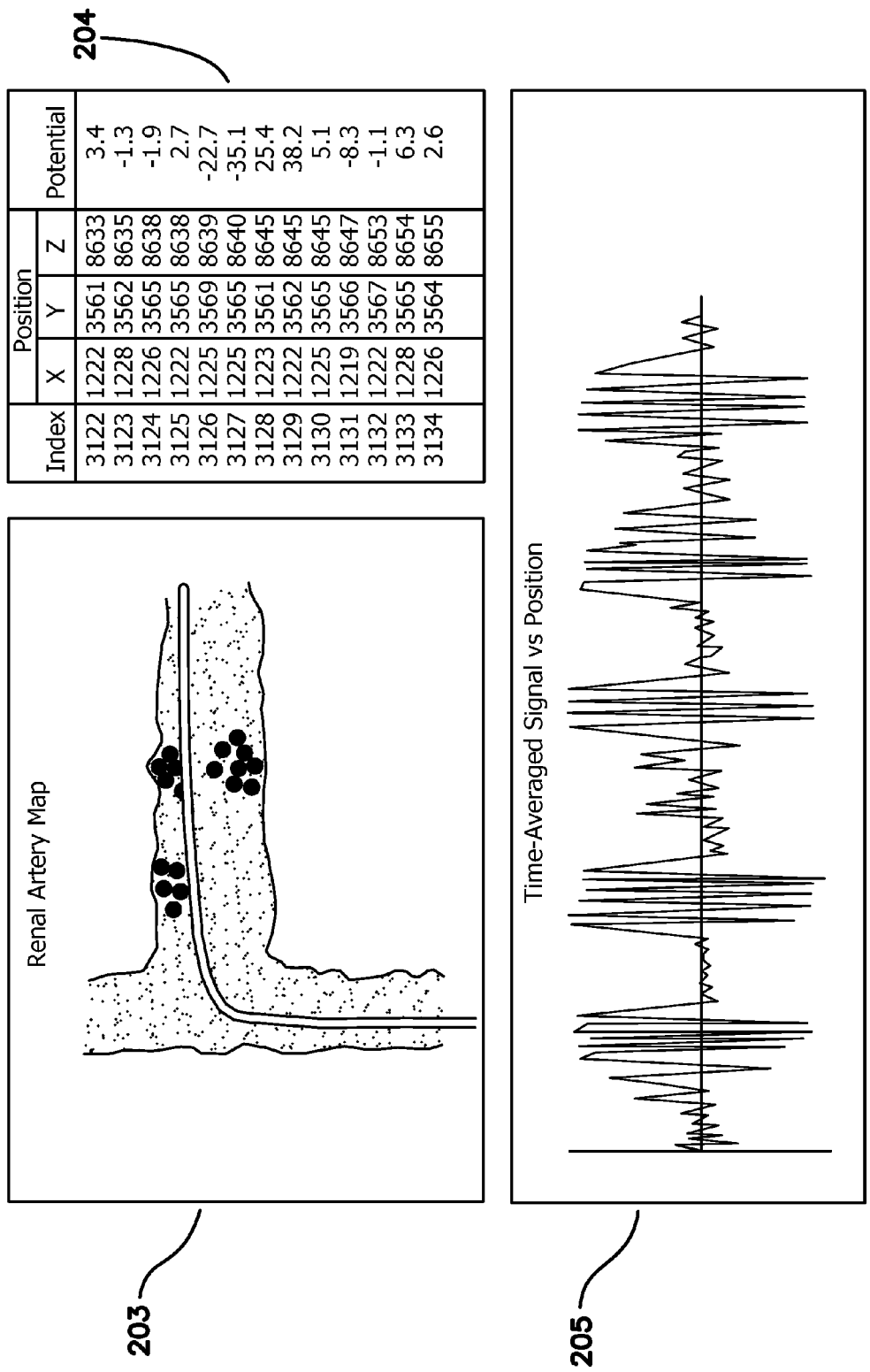
FIG. 7B is a diagram of a catheter with its MOSFET sensor array guided to the target site with a table of sensed signals and position and a graph of a time-averaged signal verses position.

FIG. 7B illustrates catheter 800 with its MOSFET sensor array 500 is guided to the target site, the catheter is first performing the electro anatomical mapping procedure where the arterial structure is identified and the bioelectric potentials 205 are recorded. The data set 204 is emulated so as to form a graphic representation of the anatomy with its associated dimensional coordinates, the bioelectrical potential values measured by the sensor modules 520 are then correlated, so as to form a data set comprising of an data set 204 (X, Y, Z, <IMPΩ>T°), and where the X, Y, Z are the coordinates of sensor module 520 from the MOSFET sensor array 500, and the value <IMPΩ> is the impedance of the site and where T° is the temperature registered at the site. The operator or physician uses the map generated by the MOSFET sensor array 500 and its graphical display so as to enable the operator to optimally proceed with the therapeutic phase of the neuromodulation.

The figure further describes graphically the renal sympathetic efferent and afferent nerves, which schematically represented adjacent to the wall of the renal artery 325, described previously in FIG. 7. The importance of proper mapping of the axonal terminus of the nerve lying in and within the renal nerves in patients with hypertension can now be defined with the disclosed development of percutaneous minimally invasive mapping apparatus 600, coupling such precise identification by the MOSFET sensor array 500 with the use of an RF energy generator, the operator can improve the procedure of neuromodulation (renal denervation). The use of the disclosed MOSFET sensor array 500, enables the formation of an accurate spatio-temporal definition of the electro-anatomical characteristics of the renal artery nerve endings. The embodiments of the disclosed apparatus 600 are directly related to the nature of the sensor module 520 due to its ability to collect electrical data in the order of 0.1 micro-volts.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

We claim:

1. An apparatus for making a temporal, spatial electro-anatomical map of bioelectrically active tissue with fidelity and accuracy depicting a local electrogram with native dynamics while simultaneously including geometric and time domain specificity comprising:
    a catheter with a MOSFET sensor array for the detection of a bioelectric potential with each sensor of the MOSFET sensor array having a MOSFET locally disposed in or on the catheter proximate to a corresponding sensor pad, and wherein each sensor mimics a sensed biopotential via a variable resistor, a local amplifier and a ground potential which is set locally within a contact between a cell of the bioelectrically active tissue and the corresponding sensor pad;
    where the MOSFET sensor array detects a plurality of bioelectric potentials in the bioelectrically active tissue at a plurality of selectively chosen sites in the bioelectrically active tissue at a plurality of times;
    a memory for storing the detected plurality of bioelectric potentials and locations of the corresponding selectively chosen sites for each of the plurality of times; and
    a processor coupled to the MOSFET sensor array for differentiating between "near" and "far field" signals at each of the corresponding MOSFET sensors of the MOSFET sensor array, and for constructing the temporal, spatial electro-anatomical map of the bioelectrically active tissue from the stored plurality of bioelectric potentials and locations of the corresponding selectively chosen sites and plurality of times.

2. The apparatus of claim 1 where each sensor of the MOSFET sensor array comprises a MOSFET isolated junction to measure action potentials without the parasitic capacitive or resistive loads with at least 0.1 µV sensitivity.

3. The apparatus of claim 1 where each sensor of the MOSFET sensor array comprises a MOSFET isolated junction with a high impedance and low capacitance semiconductor sensing element to eliminate double-layer ionic transfer and conductive charge injection effects.

4. The apparatus of claim 1 where each sensor of the MOSFET sensor array comprises an integrated MOSFET isolated junction with a differential output with high noise immunity and low static power consumption with static CMOS gates to dissipate nearly zero power when idle and to avoid injection of noise to the bioelectrically active tissue.

5. The apparatus of claim 1 further comprising a sensor for detecting nonelectrical biosignals simultaneously with the bioelectric potentials, where both the nonelectrical biosignals and bioelectric potentials are stored in the memory, and where the processor constructs a boundary condition map of the bioelectrically active tissue from the stored plurality of bioelectric potentials, nonelectrical biosignals and locations of the corresponding selectively chosen sites, and generates a comparative boundary condition and electro-anatomical map to allow for physician diagnosis.

6. The apparatus of claim 5 where each sensor of the MOSFET sensor array is capacitive with a specific dielectric interface between each sensor of the MOSFET sensor array and the bioelectrically active tissue depending on the tissue and where the processor constructs the boundary condition and bioelectric signal maps for the specific dielectric interface with selected baseline constants of a dielectric coefficient for a specific tissue.

7. The apparatus of claim 1 where each MOSFET sensor of the MOSFET sensor array includes an amplifier with a DC to at least a 1 kHz bandwidth, with at least 95 dB common mode rejection, and at least 0.1 µV sensitivity.

8. An apparatus for making a temporal, spatial electro-anatomical map of bioelectrically active tissue characterized by a temporal biopotential generated by a plurality of cells, the temporal, spatial electro-anatomical map depicting a local electrogram with native dynamics with fidelity and accuracy while simultaneously including geometric and time domain specificity comprising:
a catheter;
a plurality of sensing pads on or in the catheter organized with a bipolar, quadripolar, decapolar, or multi-electrode basket-type geometry;
a local MOSFET sensor circuit array in or on the catheter at or near the plurality of sensing pads and coupled to the plurality of sensing pads for the real time detection of bioelectric potential of adjacent bioelectrically active tissue with a plurality of electrodes MOSFET sensor circuit array comprising a plurality of sensor circuits, each of which mimic sensed biopotential via a variable resistor, a local amplifier and a ground potential which is configured to be set locally within a contact between a cell and a corresponding pad; and
a processor for constructing the temporal, spatial electro-anatomical map of the bioelectrically active tissue from the plurality of sensing pads.

9. The apparatus of claim 8 further comprising a balloon having a surface, where the plurality of sensing pads are organized as a collapsible basket on or in the balloon surface and/or carried by a plurality of expandable arms disposed on or in the balloon surface.

10. The apparatus of claim 9 wherein the apparatus comprises the plurality of expandable arms disposed on or in the balloon surface and wherein each MOSFET sensor circuit of the MOSFET sensor circuit array is disposed on or in one of the plurality of expandable arms and coupled to at least one adjacent electrode of the plurality of electrodes.

11. The apparatus of claim 8 where the local MOSFET sensor circuit array detects biopotential signals with at least 0.1 µV sensitivity or less and with a 25 kHz or higher sampling rate.

12. The apparatus of claim 8 where the plurality of sensing pads are configured in a geometry on the catheter adapted to sense biopotentials of bioelectrically active renal tissue.

13. The apparatus of claim 8 where the plurality of pads are configured in a geometry on the catheter adapted to sense biopotentials of bioelectrically active brain tissue.

\* \* \* \* \*